United States Patent
Rodgers et al.

(10) Patent No.: US 12,102,623 B2
(45) Date of Patent: *Oct. 1, 2024

(54) COMPOSITIONS FOR THE TREATMENT OF HYPERTENSION

(71) Applicant: THE GEORGE INSTITUTE FOR GLOBAL HEALTH, Newtown (AU)

(72) Inventors: Anthony Rodgers, Newtown (AU); Stephen MacMahon, Newtown (AU)

(73) Assignee: THE GEORGE INSTITUTE FOR GLOBAL HEALTH, Sydney (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/932,982

(22) Filed: Sep. 16, 2022

(65) Prior Publication Data
US 2023/0087834 A1    Mar. 23, 2023

Related U.S. Application Data

(63) Continuation of application No. 17/014,358, filed on Sep. 8, 2020, now Pat. No. 11,478,462, which is a continuation of application No. 16/393,774, filed on Apr. 24, 2019, now Pat. No. 10,799,487, which is a continuation of application No. 15/919,923, filed on Mar. 13, 2018, now Pat. No. 10,322,117, which is a continuation of application No. PCT/IB2018/000083, filed on Jan. 23, 2018.

(60) Provisional application No. 62/450,324, filed on Jan. 25, 2017.

(51) Int. Cl.
A61K 31/4422    (2006.01)
A61K 31/277     (2006.01)
A61K 31/382     (2006.01)
A61K 31/40      (2006.01)
A61K 31/4035    (2006.01)
A61K 31/404     (2006.01)
A61K 31/41      (2006.01)
A61K 31/4178    (2006.01)
A61K 31/4184    (2006.01)
A61K 31/4418    (2006.01)
A61K 31/495     (2006.01)
A61K 31/517     (2006.01)
A61K 31/549     (2006.01)
A61K 31/554     (2006.01)
A61P 9/12       (2006.01)

(52) U.S. Cl.
CPC ........ A61K 31/4422 (2013.01); A61K 31/277 (2013.01); A61K 31/382 (2013.01); A61K 31/40 (2013.01); A61K 31/4035 (2013.01); A61K 31/404 (2013.01); A61K 31/41 (2013.01); A61K 31/4178 (2013.01); A61K 31/4184 (2013.01); A61K 31/4418 (2013.01); A61K 31/495 (2013.01); A61K 31/517 (2013.01); A61K 31/549 (2013.01); A61K 31/554 (2013.01); A61P 9/12 (2018.01)

(58) Field of Classification Search
CPC .............. A61K 2300/00; A61K 31/277; A61K 31/382; A61K 31/40; A61K 31/4035; A61K 31/404; A61K 31/41; A61K 31/4178; A61K 31/4184; A61K 31/4418; A61K 31/4422; A61K 31/495; A61K 31/517; A61K 31/549; A61K 31/554; A61P 9/12
See application file for complete search history.

(56) References Cited

U.S. PATENT DOCUMENTS

| | | | |
|---|---|---|---|
| 10,322,117 B2 | 6/2019 | Rodgers et al. | |
| 10,369,156 B2 | 8/2019 | Rodgers et al. | |
| 10,799,487 B2 | 10/2020 | Rodgers et al. | |
| 11,478,462 B2 | 10/2022 | Rodgers et al. | |
| 2003/0175344 A1 | 9/2003 | Wald et al. | |
| 2003/0199492 A1 | 10/2003 | Scott | |
| 2004/0198789 A1 | 10/2004 | Leonardi et al. | |
| 2005/0187262 A1 | 8/2005 | Grogan et al. | |
| 2007/0191438 A1 | 8/2007 | Rohrer | |
| 2007/0293552 A1 | 12/2007 | Gorczynski | |
| 2008/0096866 A1 | 4/2008 | Woo et al. | |
| 2009/0099241 A1 | 4/2009 | Shetty et al. | |
| 2012/0034272 A1 | 2/2012 | Kuhl et al. | |
| 2012/0115854 A1 | 5/2012 | Shetty et al. | |
| 2013/0210778 A1 | 8/2013 | Wald et al. | |
| 2014/0206674 A1* | 7/2014 | Zwickl | A61K 31/4178 514/394 |
| 2016/0213694 A1* | 7/2016 | Kumar | A61K 31/415 |
| 2018/0133227 A1* | 5/2018 | Rodgers | A61P 7/10 |
| 2020/0030296 A1 | 3/2020 | Rodgers et al. | |

(Continued)

FOREIGN PATENT DOCUMENTS

CN   101450211 A   6/2009
CN   101618215 A   1/2010

(Continued)

OTHER PUBLICATIONS

Glezer et al. Comparative analysis of the effectiveness of diuretic in the treatment of arterial hypertension in women. The results of the Athena study. Problems of Women's Health 2(4):5-16 (2009).

(Continued)

Primary Examiner — Umamaheswari Ramachandran
(74) Attorney, Agent, or Firm — WILSON SONSINI GOODRICH & ROSATI

(57) ABSTRACT

Provided herein are pharmaceutical compositions that are useful for the treatment of hypertension comprising an angiotensin II receptor blocker, a diuretic, and a calcium channel blocker.

12 Claims, 3 Drawing Sheets

(56) References Cited

U.S. PATENT DOCUMENTS

| | | |
|---|---|---|
| 2023/0125076 A1 | 4/2023 | Rodgers et al. |
| 2023/0381161 A1 | 11/2023 | Rodgers et al. |

FOREIGN PATENT DOCUMENTS

| | | |
|---|---|---|
| CN | 101966187 A | 2/2011 |
| CN | 101966190 A | 2/2011 |
| CN | 102225203 A | 10/2011 |
| CN | 102327272 B | 8/2013 |
| CN | 106310278 A | 1/2017 |
| EP | 1272220 B1 | 5/2006 |
| EP | 2575808 A1 | 4/2013 |
| KR | 20090057538 A | 6/2009 |
| WO | WO-03097045 A1 | 11/2003 |
| WO | WO-2007098390 A2 | 8/2007 |
| WO | WO-2007109037 A2 | 9/2007 |
| WO | WO-2007146900 A2 | 12/2007 |
| WO | WO-2009026517 A2 | 2/2009 |
| WO | WO-2010127099 A2 | 11/2010 |
| WO | WO-2011149438 A1 | 12/2011 |
| WO | WO-2014114627 A1 | 7/2014 |
| WO | WO-2017054787 A1 | 4/2017 |
| WO | WO-2018091967 A1 | 5/2018 |
| WO | WO-2018138578 A1 | 8/2018 |
| WO | WO-2020021341 A1 | 1/2020 |

OTHER PUBLICATIONS

Kharkevich. Pharmacology 3rd ed. Revised and supplemented,—M: Medicine p. 34 (1987).
Kirichenko. The angiotensin II receptor antagonist candesartan in the arsenal of the therapist. Consilium Medicum 18:76-80 (2016).
Krosnyuk et al. Pharmaceutical technology: Technology of dosage forms: textbook. for stud. higher. study institutions 2nd ed. stereo—M.: Publishing Center "Academia". p. 6 (2006).
Morozova et al. Clinical and economic aspects of the use of statins in patients with arterial hypertension with lipid metabolism disorders. Quality Clinical Practice 3:66-70 (2008).
Shilov. III-generation calcium channel blockers in the treatment of arterial hypertension. Systemic hypertension 3:38-42 (2013).
Amlodipine Besylate Tablets. Greenstone Brand. NDS 19-787/S-042 (14 pgs) (2007).
Andren et al. Enalapril with either a "very low" or "low" dose of hydrochlorothiazide is equally effective in essential hypertension: a double-blind trial in 100 hypertensive patients. J Hypertension I(suppl2):384-386 (1983).
Anonymous. Assessment Report for Exforge HCT. European Medicines Agency. Evaluation of Medicines for Humane Use. Retrieved from the Internet: URL:https://www.ema.europa.eu/en/documents/assessment-report/exforge-hct-epar-public-assessment-report_en.pdf (2009).
Anonymous. Triple Therapy Prevention of Recurrent Intracerebral Disease EveNts Trial. clinicaltrials.gov (Mar. 4, 2016). Retrieved from the Internet: URL:https://clinicaltrials.gov/ct2/show/record/NCT02699645?view=record.
Australian Institute of Health and Welfare 2017. Medicines for cardiovascular disease. Cat. No. CVD 80. Canberra: AIHW box 4 (36 pgs.) (2017).
Beall et al. Could patents interfere with the development of a cardiovascular polypill? J Transl Med 14:242 (2016).
Berge et al. Pharmaceutical Salts. Journal of Pharmaceutical Sciences 66(1):1-19 (Jan. 1977).
Bisoprolol/hydrochlorothiazide (Rx). Medscape Drugs & Diseases. Available at https://reference.medscape.com/drug/ziac-bisoprolol-hydrochlorothiazide-999421 (retrieved Dec. 18, 2020).
ClinicalTrials.gov. Study to Evaluate the Efficacy and Safety of Telmisartan/Amlodipine/Rosuvastatin. [retrieved from internet on Nov. 11, 2019] URL:<https://clinicaltrials.gov/ct2/show/NCT03088254> First Posted Mar. 23, 2017.
ClinicalTrials.gov. The SCCS Polypill Pilot Trial. [retrieved from internet on Nov. 19, 2019] URL:https://clinicaltrials.gov/ct2/show/NCT02278471; First Posted Oct. 30, 2014.
ClinicalTrials.gov. Triple Therapy Prevention of Recurrent Intracerebral Disease EveNts Trial (TRIDENT). [retrieved from internet on Apr. 12, 2018] URL:https://clinicaltrials.gov/ct2/show/results/NCT02699645; First posted Mar. 4, 2016.
Crestor (rosuvastatin calcium) tablets drug label. Initial U.S. Approval: 2003. Reference ID: 3937746. May 2016.
Diabetes Educational Services. Available at https://diabetesed.net/page/_files/Antihypertensive-Meds-2012.pdf (3 pgs.) (2012).
Dinicolantonio et al. Evidence-based diuretics: focus on chlorthalidone and indapamide. Future Cardiology 11:203-217 (2015).
Drug Dosage. https://www.drugs.com/dosage/ (3 pgs.) (Accessed Apr. 2018).
Emc+ Compendium. Latest Medicine Updates. https://www.medicines.org.uk/emc (2 pgs.) (Accessed Apr. 2018).
Fishbane et al. Iron deficiency in non-dialysis chronic kidney disease. Kidney Int 75:752-754 (2008).
Fletcher et al. Efficacy of drug therapy in the secondary prevention of cardiovascular disease and stroke. Am J Cardiol. 99(6C):1E-35E (2007).
Huffman et al. Low-Dose Combination Blood Pressure Pharmacotherapy to Improve Treatment Effectiveness, Safety and Efficiency. JAMA 320(6):552-554 (2018).
Huo et al. Effect of Simvastatin on Ankle Brachial Index in Middle and Old Age Patients with Hypertension. China Pharmacy 24(40):3795-3796 (2013) (English Abstract).
Kenward et al. An improved approximation to the precision of fixed effects from restricted maximum likelihood. Computational Statistics & Data Analysis 53(7): 2583-2595 (2009).
Kenward et al. The use of baseline covariates in crossover studies. Biostatistics 11(1):1-17 (2010).
Kuriyama et al. Renoprotective effect of triple therapy with low-dose angiotensis receptor blocker, low-dose diuretic and Ca-antagonist in hypertensive type-2 diabetic patients with overt nephropathy. Japanese Journal of Nephrology 45:367-371 (2003) (English Translation included).
Law et al. Lowering blood pressure to prevent myocardial infarction and stroke: a new preventive strategy. Health Technology Assessment 7(31):1-105 (2003).
Law et al. Value of low dose combination treatment with blood pressure lowering drugs: analysis of 354 randomised trials. BMJ 326(7404):1427 (2003).
Lee et al. A Randomized, Multicenter, Double-blind, Placebo-controlled Study to Evaluate the Efficacy and the Tolerability of a Triple Combination of Amlodipine/Losartan/Rosuvastatin in Patients With Comorbid Essential Hypertension and Hyperlipidemia. Clinical Therapeutics 39(12):2366-2379 (2017).
Liu et al. Should baseline be a covariate or dependent variable in analyses of change from baseline in clinical trials? Stat Med 28(20):2509-2530 (2009).
Lozol® Indapamide Tablets. Aventis Pharmaceuticals Inc. (8 pgs.) (2005).
Mahmud et al. Low-dose quadruple antihypertensive combination: more efficacious than individual agents—a preliminary report. Hypertension 49:272-275 (2007).
Maladkar et al. Triple drug combination of telmisartan, amlodipine and hydrochlorothiazide in the treatment of essential hypertension. Open Journal of Internal Medicine 2:67-71 (2012).
Mallion et al. ABPM comparison of the antihypertensive profiles of the selective angiotensin II receptor antagonists telmisartan and losartan in patients with mild-to-moderate hypertension. J Hum Hypertens 13:657-664 (1999).
Micardis (Telmisartan) Tablets. Boehringer Ingelheim. NDA 20-850/S-022/S-023 (12 pgs.) (2009).
Neutel et al. Comparison of Monotherapy with Irbesartan 150 mg or Amlodipine 5 mg for Treatment of Mild-to-Moderate Hypertension. J Renin-Angiotensin_Aldosteone System 6(2):84-89 (2005).
Nickenig. Should Angiotensin II Receptor Blockers and Statins Be Combined? Circulation 10:1013-1020 (2004).
O'Brien et al. Ambulatory Blood Pressure Measurement. What Is the International Consensus? Hypertension 62(6):988-994 (2013).

(56) References Cited

OTHER PUBLICATIONS

PCT/IB2017/001524 International Search Report and Written Opinion dated Apr. 17, 2018.
PCT/IB2018/000083 International Search Report and Written Opinion dated Apr. 24, 2018.
PCT/IB2019/000923 International Search Report and Written Opinion dated Dec. 2, 2019.
Pinto et al. Lessons from rat models of hypertension: from Goldblatt to genetic engineering. Cardiovascular Res 39(1):77-88 (1998).
RxList. https://www.rxlist.com (5 pgs.) (Accessed Apr. 2018).
Salam et al. TRIple pill vs Usual care Management for Patients with mild-to-moderate Hypertension (TRIUMPH): Study protocol. Am Heart J. 167(2):127-132 (2014).
Sharma. Dr. Reddy's launches combo drug for hypertension. Available at https://www.businesstoday.in/industry/pharma/story/dr-reddys-launches-combo-drug-for-hypertension-135017-2014-01-10 (2014).
Skoularigis et al. Low dose hydrochlorothiazide (12.5 to 25 mg daily) as monotherapy in black patients with mild to moderate hypertension. Assessment by ambulatory blood pressure monitoring. Am J Hypertens 8(10 Pt 1):1046-1050 (1995) (Abstract only).
Smith et al. Comparison of telmisartan versus losartan: meta-analysis of titration-to-response studies. Blood Pressure Monitoring 8(3):111-117 (2003).
Spinler et al. ACE inhibitors versus ARBs: comparison of practice guidelines and treatment selection considerations. Formulary 41:274-284 (2006).
Sureja et al. Development and validation of HPTLC method for simultaneous estimation of telmisartan and indapamide in pharmaceutical solid dosage form. Journal of Chemical and Pharmaceutical Research 7:236-240 (2015).
Tandon et al. Antihypertensive drug prescription patterns, rationality, and adherence to Joint National Committee-7 hypertension treatment guidelines among Indian postmenopausal women. J Mid-life Health 5(2):78-83 (2014).
Triple Therapy Prevention of Recurrent Intracerebral Disease EveNts Trial (TRIDENT). Available at https://clinicaltrials.gov/ct2/show/record/NCT02699645. First posted Mar. 4, 2016 (16 pgs).
Triple Therapy Prevention of Recurrent Intracerebral Disease EveNts Trial (TRIDENT). Available at https://clinicaltrials.gov/ct2/show/record/NCT02699645. First posted Mar. 4, 2016 (Latest version Oct. 2, 2018) (9 pgs).
U.S. Appl. No. 15/352,425 Office Action dated May 5, 2017.
U.S. Appl. No. 15/352,425 Office Action dated Nov. 30, 2017.
U.S. Appl. No. 15/919,923 Office Action dated Aug. 15, 2018.
U.S. Appl. No. 15/919,923 Office Action dated Nov. 15, 2018.
U.S. Appl. No. 16/393,774 Office Action dated Jan. 15, 2020.
U.S. Appl. No. 16/523,230 Office Action dated Jan. 8, 2021.
U.S. Appl. No. 16/523,230 Office Action dated Jun. 21, 2022.
U.S. Appl. No. 16/523,230 Office Action dated Nov. 8, 2021.
U.S. Appl. No. 17/014,358 Office Action dated Dec. 16, 2021.
Volpe et al. Rationale for triple fixed-dose combination therapy with an angiotensin II receptor blocker, a calcium channel blocker, and a thiazide diuretic. Vasc Health Risk Manag 8:371-380 (2012).
Wald et al. Combination therapy versus monotherapy in reducing blood pressure: meta-analysis on 11,000 participants from 42 trials. Am J Med 122(3):290-300 (2009).
Wald et al. Randomized Polypill crossover trial in people aged 50 and over. PLoS One 7(7):e41297 (2012).
Webster et al. Fixed Low-Dose Triple Combination Antihypertensive Medication vs Usual Care for Blood Pressure Control in Patients With Mild to Moderate Hypertension in Sri Lanka: A Randomized Clinical Trial. JAMA 320(6):566-579 (2018).
Webster. Protocol changes to the TRIUMPH study. Am Heart J 191:e1 (2017).
Chou. Drug Combination Studies and Their Synergy Quantification Using the Chou-Talalay Method. Cancer Res 70(2):440-446 (2010).
Higaki et al. Effect of hydrochlorothiazide in addition to telmisartan/amlodipine combination for treating hypertensive patients uncontrolled with telmisartan/amlodipine: a randomized, double-blind study. Hypertens Res 40(3):251-258 (2017).
Jadhav et al. Blood pressure control with a single-pill combination of indapamide sustained-release and amlodipine in patients with hypertension: the EFFICIENT study. PLoS One 9(4):e92955 (2014).
Mashkovsky M.D. Medicines: In 2 vols. V. 1.—M.: New Wave Publishing House LLC, 540:11 (2021).
Ohira et al. Comparisons of Increasing Calcium Channel Blocker dose and Adding Thiazide Diuretic in Hypertensive Patients Given Medium-dose Angiotensin II Receptor Blocker and Amlodipine. Dokkyo Journal of Medical Sciences 44(3):209-216 (2017).
Vengerovsky, A.I. Pharmacological incompatibility. Bulletin of Siberian Medicine 3:49-56.

* cited by examiner

COMPOSITIONS FOR THE TREATMENT OF HYPERTENSION

CROSS REFERENCE

This application is a continuation of U.S. application Ser. No. 17/014,358, filed Sep. 8, 2020, which is a continuation of U.S. application Ser. No. 16/393,774, filed Apr. 24, 2019, now U.S. Pat. No. 10,799,487, issued Oct. 13, 2020, which is a continuation of U.S. application Ser. No. 15/919,923, filed Mar. 13, 2018, now U.S. Pat. No. 10,322,117, issued Jun. 18, 2019, which is a continuation of International Application No. PCT/IB2018/000083, filed Jan. 23, 2018, which claims the benefit of U.S. Provisional Application No. 62/450,324, filed Jan. 25, 2017, each of which are hereby incorporated by reference in their entirety.

BACKGROUND OF THE DISCLOSURE

High blood pressure, also known as hypertension, is a leading cause of preventable morbidity and mortality and it is well established that treatments that lower blood pressure (BP) are beneficial. However, despite the plethora of blood pressure lowering medicines available, many patients continue to have poor blood pressure control as evidenced by multiple large-scale population studies. Contributing factors for poor blood pressure control include poor adherence, complex guidelines recommending multiple up-titration steps, and treatment inertia. Furthermore, the majority of treated patients receive only monotherapy, which has limited potency even at high doses where side effects are increased and tolerability reduced. Accordingly, there exists a need for new treatments for lowering high blood pressure that are efficacious and tolerable.

SUMMARY OF THE DISCLOSURE

Provided herein in one aspect is a pharmaceutical composition comprising
 (a) an angiotensin II receptor blocker;
 (b) a diuretic; and
 (c) a calcium channel blocker
wherein the dose of each (a), (b), and (c) is from about 40% to about 80% of the lowest hypertension therapeutic dose (LHTD) for each of the (a), (b), and (c).

In some embodiments, the pharmaceutical composition is essentially free of an angiotensin-converting enzyme inhibitor or a pharmaceutically acceptable salt thereof, a beta-blocker or a pharmaceutically acceptable salt thereof, a lipid-regulating agent, platelet function-altering agent, a serum homocysteine-lowering agent, or a combination thereof.

In some embodiments, the diuretic is a thiazide-like diuretic. In some embodiments, the thiazide-like diuretic is quinethazone, clopamide, chlorthalidone, mefruside, clofenamide, metolazone, meticrane, xipamide, indapamide, clorexolone, fenquizone, or the pharmaceutically acceptable salt or hydrate thereof. In some embodiments, the thiazide-like diuretic is indapamide or the hydrate thereof. In some embodiments, the thiazide-like diuretic is indapamide.

In some embodiments, the calcium channel blocker is amlodipine, nifedipine, diltiazem, nimodipine, verapamil, isradipine, felodipine, nicardipine, nisoldipine, clevidipine, dihydropyridine, lercanidipine, nitrendipine, cilnidipine, manidipine, mibefradil, bepridil, barnidipine, nilvadipine, gallopamil, lidoflazine, aranidipine, dotarizine, diproteverine, or the pharmaceutically acceptable salt or hydrate thereof. In some embodiments, the calcium channel blocker is amlodipine or the pharmaceutically acceptable salt thereof. In some embodiments, the calcium channel blocker is amlodipine besylate.

In some embodiments, the angiotensin II receptor blocker is irbesartan, telmisartan, valsartan, candesartan, eprosartan, olmesartan, azilsartan, losartan, or the pharmaceutically acceptable salt or hydrate thereof. In some embodiments, the angiotensin II receptor blocker is telmisartan.

In some embodiments, the dose of each (a), (b), and (c) is from about 40% to about 60% of the lowest hypertension therapeutic dose (LHTD) for each of the (a), (b), and (c). In some embodiments, the diuretic is a thiazide-like diuretic, and the dose of the thiazide-like diuretic is about 50% of the lowest hypertension therapeutic dose (LHTD) for the thiazide-like diuretic. In some embodiments, the thiazide-like diuretic is indapamide, and the dose of the indapamide is about 0.625 mg. In some embodiments, the dose of the calcium channel blocker is about 50% of the lowest hypertension therapeutic dose (LHTD) for the calcium channel blocker. In some embodiments, the calcium channel blocker is amlodipine besylate, and the dose of amlodipine besylate is about 1.25 mg. In some embodiments, the dose of the angiotensin II receptor blocker is about 50% of the lowest hypertension therapeutic dose (LHTD) for the angiotensin II receptor blocker. In some embodiments, the angiotensin II receptor blocker is telmisartan, and the dose of the telmisartan is about 10 mg. In some embodiments, the angiotensin II receptor blocker is telmisartan, the diuretic is indapamide, and the calcium channel blocker is amlodipine besylate. In some embodiments, the dose of telmisartan is from about 8 mg to about 12 mg, the dose of indapamide is from about 0.5 mg to about 0.75 mg, and the dose of amlodipine besylate is from about 1 mg to about 1.5 mg. In some embodiments, the dose of telmisartan is about 10 mg, the dose of indapamide is about 0.625 mg, and the dose of amlodipine besylate is about 1.25 mg.

Provided in another aspect is a pharmaceutical composition comprising
 (a) telmisartan;
 (b) a thiazide-like diuretic; and
 (c) a calcium channel blocker
wherein the dose of each (a), (b), and (c) is from about 80% to about 150% of the lowest hypertension therapeutic dose (LHTD) for each of the (a), (b), and (c).

In some embodiments, the pharmaceutical composition is essentially free of an angiotensin-converting enzyme inhibitor or a pharmaceutically acceptable salt thereof, a beta-blocker or a pharmaceutically acceptable salt thereof, a lipid-regulating agent, platelet function-altering agent, a serum homocysteine-lowering agent, or a combination thereof.

In some embodiments, the thiazide-like diuretic is quinethazone, clopamide, chlorthalidone, mefruside, clofenamide, metolazone, meticrane, xipamide, indapamide, clorexolone, fenquizone, or the pharmaceutically acceptable salt or hydrate thereof. In some embodiments, the thiazide-like diuretic is indapamide or the hydrate thereof. In some embodiments, the thiazide-like diuretic is indapamide.

In some embodiments, the calcium channel blocker is amlodipine, nifedipine, diltiazem, nimodipine, verapamil, isradipine, felodipine, nicardipine, nisoldipine, clevidipine, dihydropyridine, lercanidipine, nitrendipine, cilnidipine, manidipine, mibefradil, bepridil, barnidipine, nilvadipine, gallopamil, lidoflazine, aranidipine, dotarizine, diproteverine, or the pharmaceutically acceptable salt or hydrate thereof. In some embodiments, the calcium channel blocker is amlodipine or the pharmaceutically acceptable salt thereof. In some embodiments, the calcium channel blocker is amlodipine besylate.

In some embodiments, the dose of each (a), (b), and (c) is from about 80% to about 120% of the lowest hypertension therapeutic dose (LHTD) for each of the (a), (b), and (c). In some embodiments, the dose of the thiazide-like diuretic is about 100% of the lowest hypertension therapeutic dose (LHTD) for the thiazide-like diuretic. In some embodiments, the thiazide-like diuretic is indapamide, and the dose of the indapamide is about 1.25 mg. In some embodiments, the dose of the calcium channel blocker is about 100% of the lowest hypertension therapeutic dose (LHTD) for the calcium channel blocker. In some embodiments, the calcium channel blocker is amlodipine besylate, and the dose of amlodipine besylate is about 2.5 mg. In some embodiments, the dose of the telmisartan is about 100% of the lowest hypertension therapeutic dose (LHTD) for telmisartan. In some embodiments, the dose of the telmisartan is about 20 mg. In some embodiments, the thiazide-like diuretic is indapamide, and the calcium channel blocker is amlodipine besylate. In some embodiments, the dose of telmisartan is from about 16 mg to about 24 mg, the dose of indapamide is from about 1 mg to about 1.5 mg, and the dose of amlodipine besylate is from about 2 mg to about 3 mg. In some embodiments, the dose of telmisartan is about 20 mg, the dose of indapamide is about 1.25 mg, and the dose of amlodipine besylate is about 2.5 mg.

In some embodiments for the pharmaceutical compositions disclosed herein, (a), (b), and (c) are provided in one formulation. In some embodiments, (a), (b), and (c) are each provided in a separate formulation. In some embodiments, two of the (a), (b), and (c) are provided in one formulation. In some embodiments, the pharmaceutical composition is in the form of pill, tablet, or capsule. In some embodiments, the pharmaceutical composition is suitable for oral administration.

Also provided herein is a method of treating hypertension in a subject in need thereof comprising administering any one of the pharmaceutical compositions disclosed herein. In some embodiments, the treatment results in a systolic blood pressure (SBP) of less than about 140 mmHg. In some embodiments, the treatment results in a reduction of systolic blood pressure (SBP) of about 10 mmHg or greater. In some embodiments, the treatment results in a diastolic blood pressure (DBP) of less than about 90 mmHg. In some embodiments, the treatment results in a reduction of diastolic blood pressure (DBP) of about 5 mmHg or greater. In some embodiments, the treatment results in a reduction in systolic blood pressure (SBP) that is greater than the reduction obtained with the full lowest hypertension therapeutic dose of any one of the (a), (b), and (c) in the pharmaceutical composition. In some embodiments, the treatment results in a reduction in diastolic blood pressure (DBP) that is greater than the reduction obtained with the full lowest hypertension therapeutic dose of any one of (a), (b), and (c) in the pharmaceutical composition. In some embodiments, the treatment results in greater long term tolerability and reduced risk of side effects when compared to treatment with the full lowest hypertension therapeutic dose of any one of (a), (b), and (c) in the pharmaceutical composition. In some embodiments, the treatment is the initial or first-line treatment of hypertension. In some embodiments, the subject is not receiving any previous hypertension therapy prior to treatment.

Provided herein in another aspect is a pharmaceutical composition consisting essentially of (a) an angiotensin II receptor blocker;
(b) a diuretic; and
(c) a calcium channel blocker wherein the dose of each (a), (b), and (c) is from about 40% to about 80% of the lowest hypertension therapeutic dose (LHTD) for each of the (a), (b), and (c).

Provided herein in another aspect is a pharmaceutical composition consisting essentially of (a) an angiotensin II receptor blocker, such as telmisartan;
(b) a thiazide-like diuretic; and
(c) a calcium channel blocker wherein the dose of each (a), (b), and (c) is from about 80% to about 150% of the lowest hypertension therapeutic dose (LHTD) for each of the (a), (b), and (c). In some embodiments, the dose of each (a), (b), and (c) is from about 80% to about 120% of the lowest hypertension therapeutic dose (LHTD) for each of the (a), (b), and (c). In some embodiments, the dose of each (a), (b), and (c) is from about 90% to about 110% of the lowest hypertension therapeutic dose (LHTD) for each of the (a), (b), and (c).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
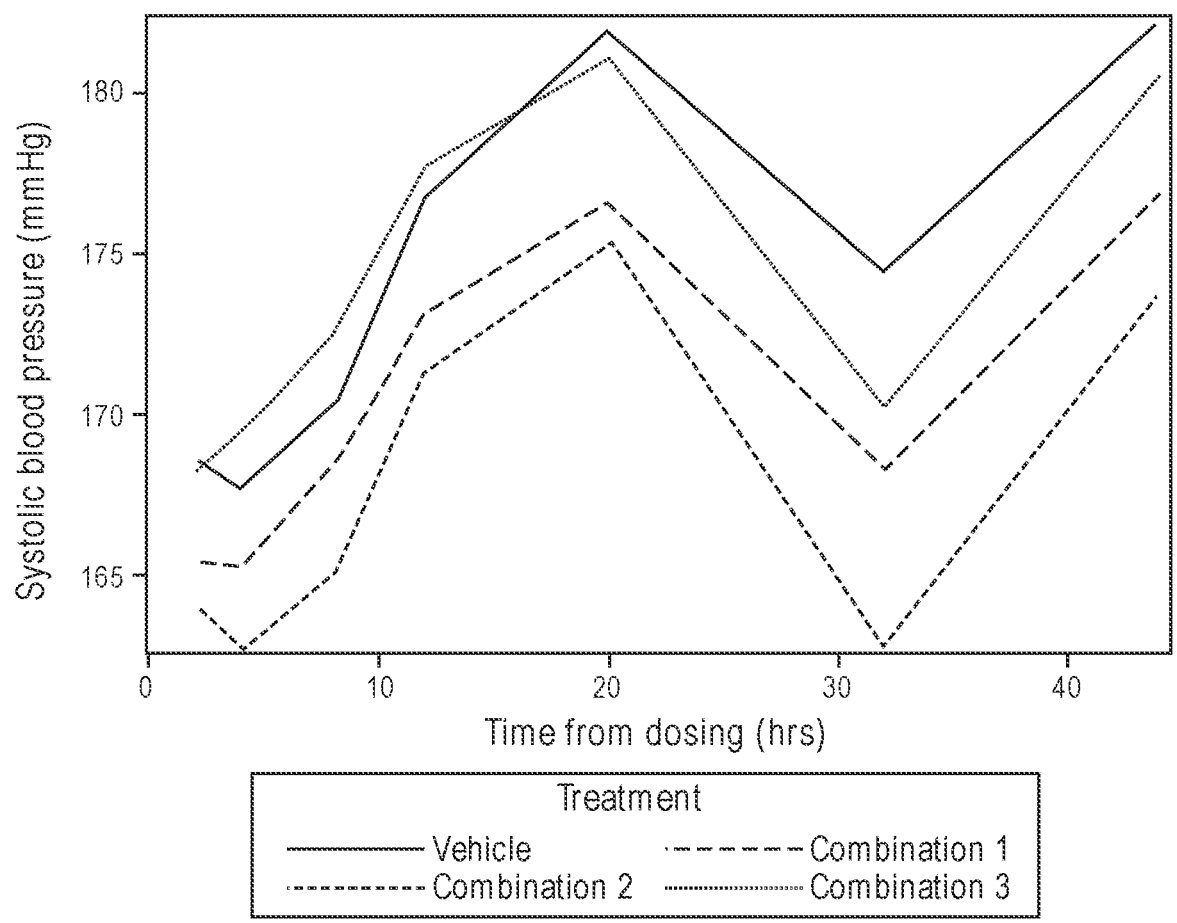
FIG. 1 shows the mean systolic blood pressure (mmHg) across time periods by treatment.

Provided herein are pharmaceutical compositions for the treatment of hypertension comprising an angiotensin II receptor blocker, a diuretic, and a calcium channel blocker. In some embodiments, the dose of each component is below the lowest dose approved for the treatment of hypertension. The present disclosure recognizes the technical effects of low-dose combination therapy set forth herein, including but not limited to, the use of low-doses to avoid or ameliorate side effects while retaining or improving benefits, the synergistic therapeutic benefits of certain drug combinations, the early introduction of combination therapy to improve therapeutic effects, etc. Described herein in one aspect are low-dose combination compositions for the treatment of hypertension, including the initial or first-line treatment of hypertension.

Certain Terminology

As used herein and in the appended claims, the singular forms "a," "and," and "the" include plural referents unless the context clearly dictates otherwise. Thus, for example, reference to "an agent" includes a plurality of such agents, and reference to "the composition" includes reference to one or more compositions (or to a plurality of compositions) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus in some embodiments, the number or numerical range varies between 1% and 10% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Pharmaceutically acceptable salt" as used herein includes both acid and base addition salts. In some embodiments, the pharmaceutically acceptable salt of any one of the compounds described herein is the form approved for use by the US Food and Drug Administration. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "hydrates" are compounds that contain either stoichiometric or non-stoichiometric amounts of water, and, in some embodiments, are formed during the process of crystallization with water. Hydrates are meant to include the hydrates of any one of the compounds described herein that is approved for use by the US Food and Drug Administration.

The term "acceptable" with respect to a formulation, composition or ingredient, as used herein, means having no persistent detrimental effect on the general health of the subject being treated.

The terms "administer," "administering," "administration," and the like, as used herein, refer to the methods that may be used to enable delivery of compounds or compositions to the desired site of biological action. These methods include, but are not limited to, oral routes, intraduodenal routes, parenteral injection (including intravenous, subcutaneous, intraperitoneal, intramuscular, intravascular or infusion), topical, and rectal administration. Those of skill in the art are familiar with administration techniques that can be employed with the compounds and methods described herein. In some embodiments, the compounds and compositions described herein are administered orally.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

Triple Compositions

Described herein are pharmaceutical compositions comprising (a) an angiotensin II receptor blocker; (b) a diuretic; and (c) a calcium channel blocker; wherein the dose of each (a), (b), and (c) is from about 40% to about 80% of the lowest hypertension therapeutic dose (LHTD) for each of the (a), (b), and (c). In some embodiments, the dose of each (a), (b), and (c) is about 40% to about 60% of the lowest hypertension therapeutic dose (LHTD) for each of the (a), (b), and (c). In some embodiments, the dose of each (a), (b), and (c) is about 50% of the lowest hypertension therapeutic dose (LHTD) for each of the (a), (b), and (c). In some embodiments, the dose of each (a), (b), and (c) is about 60% to about 80% of the lowest hypertension therapeutic dose (LHTD) for each of the (a), (b), and (c). In some embodiments, the dose of each (a), (b), and (c) is about 66% of the lowest hypertension therapeutic dose (LHTD) for each of the (a), (b), and (c).

In some embodiments, the pharmaceutical composition comprises a blood pressure-lowering combination of blood pressure-lowering active agents, wherein the blood pressure-lowering active agents consists of an angiotensin II receptor blocker, a diuretic, and a calcium channel blocker.

In another aspect described herein are pharmaceutical compositions comprising (a) an angiotensin II receptor blocker, such as telmisartan; (b) a thiazide-like diuretic; and (c) a calcium channel blocker; wherein the dose of each (a), (b), and (c) is from about 80% to about 150% of the lowest hypertension therapeutic dose (LHTD) for each of the (a), (b), and (c). In some embodiments, the dose of each (a), (b), and (c) is about 80% to about 120% of the lowest hypertension therapeutic dose (LHTD) for each of the (a), (b), and (c). In some embodiments, the dose of each (a), (b), and (c) is about 90% to about 110% of the lowest hypertension therapeutic dose (LHTD) for each of the (a), (b), and (c). In some embodiments, the dose of each (a), (b), and (c) is about 95% to about 105% of the lowest hypertension therapeutic dose (LHTD) for each of the (a), (b), and (c). In some embodiments, the dose of each (a), (b), and (c) is about 100% of the lowest hypertension therapeutic dose (LHTD) for each of the (a), (b), and (c).

In some embodiments, the pharmaceutical compositions disclosed herein are essentially free of an angiotensin-converting enzyme inhibitor (ACE inhibitor) or the pharmaceutically acceptable salt thereof. In some embodiments, the angiotensin-converting enzyme inhibitor includes, but is not limited to, benazepril, captopril, enalapril, fosinopril, lisinopril, moexipril, perindopril, quinapril, ramipril, trandolapril or the pharmaceutically acceptable salt or hydrate thereof.

Also, described herein are pharmaceutical compositions consisting essentially (a) an angiotensin II receptor blocker; (b) a diuretic; and (c) a calcium channel blocker; wherein the dose of each (a), (b), and (c) is from about 40% to about 80% of the lowest hypertension therapeutic dose (LHTD) for each of the (a), (b), and (c). In some embodiments, the dose of each (a), (b), and (c) is about 40% to about 60% of the lowest hypertension therapeutic dose (LHTD) for each of the (a), (b), and (c). In some embodiments, the dose of each (a), (b), and (c) is about 50% of the lowest hypertension therapeutic dose (LHTD) for each of the (a), (b), and (c). In some embodiments, the dose of each (a), (b), and (c) is about 60% to about 80% of the lowest hypertension therapeutic dose (LHTD) for each of the (a), (b), and (c). In some embodiments, the dose of each (a), (b), and (c) is about 66% of the lowest hypertension therapeutic dose (LHTD) for each of the (a), (b), and (c).

Also, described herein are pharmaceutical compositions consisting essentially (a) an angiotensin II receptor blocker, such as telmisartan; (b) a thiazide-like diuretic; and (c) a calcium channel blocker; wherein the dose of each (a), (b), and (c) is from about 80% to about 150% of the lowest hypertension therapeutic dose (LHTD) for each of the (a), (b), and (c). In some embodiments, the dose of each (a), (b), and (c) is about 80% to about 120% of the lowest hypertension therapeutic dose (LHTD) for each of the (a), (b), and (c). In some embodiments, the dose of each (a), (b), and (c) is about 90% to about 110% of the lowest hypertension therapeutic dose (LHTD) for each of the (a), (b), and (c). In some embodiments, the dose of each (a), (b), and (c) is about 95% to about 105% of the lowest hypertension therapeutic dose (LHTD) for each of the (a), (b), and (c). In some embodiments, the dose of each (a), (b), and (c) is about 100% of the lowest hypertension therapeutic dose (LHTD) for each of the (a), (b), and (c).

In some embodiments, the pharmaceutical compositions disclosed herein achieve a significant blood pressure reduction in a subject with modestly elevated blood pressure. In some embodiments, the pharmaceutical compositions disclosed herein achieve a significant blood pressure reduction in a subject with modestly elevated blood pressure with minimum, insignificant or no side effects.

Beta-Blockers

In some embodiments, the pharmaceutical compositions disclosed herein are essentially free of a beta blocker or the pharmaceutically acceptable salt thereof. In some embodiments, beta-blockers are compounds that inhibit the receptor sites for the endogenous catecholamines epinephrine (adrenaline) and norepinephrine (noradrenaline) on adrenergic beta receptors, of the sympathetic nervous system. In some embodiments, beta-blockers include, but are not limited to, beta-adrenergic blocking agents, beta antagonists, beta-adrenergic antagonists, beta-adrenoreceptor antagonists, or beta adrenergic receptor antagonists. In some embodiments, beta-blockers inhibit activation of all types of β-adrenergic receptors. In some embodiments, beta-blockers inhibit both β-adrenergic receptors and α-adrenergic receptors. In some embodiments, beta-blockers are selective for one of following beta receptors: β1, β2, and β3 receptors.

In some embodiments, the beta-blocker is a non-selective beta-adrenoceptor antagonist. Examples of non-selective beta-adrenoceptor antagonists include, but are not limited to, pindolol, propranolol, oxprenolol, sotalol, timolol, carteolol, penbutolol, and nadolol. In some embodiments, the beta-blocker is a compound with combined β- and α-adrenoceptor blocking action. Suitable examples include, but are not limited to, carvedilol, bucindolol and labetolol. In some embodiments, the beta-blocker is a $β_1$-selective adrenoceptor antagonist. Examples of $β_1$ selective adrenoceptor antagonist include, but are not limited to, atenolol, bisoprolol, betaxolol, metoprolol, celiprolol, esmolol, nebivolol, and acebutolol. In some embodiments, the beta blocker is $β_2$-selective adrenoceptor antagonist, such as butaxamine.

In some embodiments, the beta-blocker is acebutolol, atenolol, betaxolol, bisoprolol, carteolol, esmolol, penbutolol, metoprolol, nadolol, nebivolol, pindolol, sotalol, propranolol, carvedilol, labetalol, timolol, esmolol, celiprolol, oxprenolol, levobunolol, practolol, metipranolol, landiolol, bopindolol, pronethalol, butaxamine, bevantolol, tertatolol, arotinolol, levobetaxolol, befunolol, amosulalol, tilisolol, or the pharmaceutically acceptable salt or hydrate thereof. In some embodiments, the beta blocker is acebutolol, atenolol, betaxolol, bisoprolol, carteolol, esmolol, penbutolol, metoprolol, nadolol, nebivolol, pindolol, sotalol, propranolol, carvedilol, labetalol or the pharmaceutically acceptable salt or hydrate thereof. In some embodiments, the beta blocker is acebutolol, atenolol, betaxolol, bisoprolol, celiprolol, oxprenolol, metoprolol, nadolol, nebivolol, pindolol, propranolol, carvedilol, labetalol, timolol, or the pharmaceutically acceptable salt or hydrate thereof. In some embodiments, the beta blocker is atenolol. In some embodiments, the beta blocker is bisoprolol or the pharmaceutically acceptable salt.

Lipid-Regulating Agent

In some embodiments, the pharmaceutical compositions disclosed herein are essentially free of a lipid-regulating agent, a platelet function-altering agent, a serum homocysteine-lowering agent, or a combination thereof.

In some embodiments, the pharmaceutical compositions disclosed herein are essentially free of a lipid-regulating agent. In some embodiments, the lipid-regulating agent is a 3-hydroxy-3-methylglutaryl coenzyme A (HMG CoA) reductase inhibitor, also called a statin. In some embodiments, the lipid-regulating agent is atorvastatin, simvastatin, cerivastatin, fluvastatin, or pravastatin. In some embodiments, the lipid-regulating agent is atorvastatin or simvastatin. In some embodiments, the lipid-regulating agent is atorvastatin. In some embodiments, the lipid-regulating agent is simvastatin.

Platelet Function-Altering Agent

In some embodiments, the pharmaceutical compositions disclosed herein are essentially free of a platelet function-altering agent. In some embodiments, the platelet function-altering agent is aspirin, ticlopidine, dipyridamole, clopidogrel. In some embodiments, the platelet function-altering agent is a glycoprotein IIb/IIIa receptor inhibitor, such as abciximab. In some embodiments, the platelet function-altering agent is a non-steroidal anti-inflammatory drug, such as ibuprofen. In some embodiments, the platelet function-altering agent is aspirin, ticlopidine, dipyridamole, clopidogrel, abciximab, or ibuprofen. In some embodiments, the platelet function-altering agent is aspirin.

Serum Homocysteine-Lowering Agent

In some embodiments, the pharmaceutical compositions disclosed herein are essentially free of a serum homocysteine-lowering agent. In some embodiments, the serum homocysteine-lowering agent is folic acid, vitamin B6, or vitamin B12, or a combination thereof. In some embodiments, the serum homocysteine-lowering agent is folic acid.

Angiotensin II Receptor Antagonist/Blocker

As used herein, angiotensin II receptor antagonists or blockers (ARBs) are compounds that modulate the action of angiotensin II by preventing angiotensin II from binding to angiotensin II receptors on the muscles surrounding blood vessels. In some embodiments, the angiotensin II receptor blocker is losartan, valsartan, candesartan, eprosartan, irbesartan, telmisartan, or the pharmaceutically acceptable salt or hydrate thereof. In some embodiments, the angiotensin II receptor blocker is losartan. In some embodiments, the angiotensin II receptor blocker is valsartan. In some embodiments, the angiotensin II receptor blocker is candesartan. In some embodiments, the angiotensin II receptor blocker is eprosartan. In some embodiments, the angiotensin II receptor blocker is irbesartan. In some embodiments, the angiotensin II receptor blocker is telmisartan.

Diuretics

As used herein, diuretics refer to compounds that increase urinary flow rate. Diuretics are classified by chemical structure (thiazide diuretics and thiazide-like diuretics), site of action (such as loop diuretic), or pharmacologic effect (such as osmotic diuretics, carbonic anhydrase inhibitors, and potassium sparing diuretics).

In some embodiments, the pharmaceutical compositions disclosed herein comprise a thiazide diuretic. In some embodiments, the pharmaceutical compositions disclosed herein comprise a thiazide-like diuretic. In some embodiments, the pharmaceutical compositions disclosed herein comprise a loop diuretic. In some embodiments, the pharmaceutical compositions disclosed herein comprise an osmotic diuretic. In some embodiments, the pharmaceutical compositions disclosed herein comprise a carbonic anhydrase inhibitor. In some embodiments, the pharmaceutical compositions disclosed herein comprise a potassium sparing diuretic.

Thiazide Diuretics

As used herein, thiazide diuretics refer to compounds that contain the benzothiadiazine molecular structure. In some embodiments, thiazide diuretics inhibit sodium and chloride reabsorption in the distal tubule of the kidney, which results in increased urinary excretion of sodium and water. Examples of thiazide diuretics include, but are not limited to, altizide, bendroflumethiazide, chlorothiazide, cyclopenthiazide, cyclothiazide, epitizide, hydrochlorothiazide, hydroflumethiazide, mebutizide, methyclothiazide, polythiazide, and trichlormethiazide.

In some embodiments, the thiazide diuretic is altizide, bendroflumethiazide, chlorothiazide, cyclopenthiazide, cyclothiazide, epitizide, hydrochlorothiazide, hydroflumethiazide, mebutizide, methyclothiazide, polythiazide, trichlormethiazide, or the pharmaceutically acceptable salt or hydrate thereof. In some embodiments, the thiazide diuretic is altizide. In some embodiments, the thiazide diuretic is bendroflumethiazide. In some embodiments, the thiazide diuretic is chlorothiazide. In some embodiments, the thiazide diuretic is cyclopenthiazide. In some embodiments, the thiazide diuretic is cyclothiazide. In some embodiments, the thiazide diuretic is epitizide. In some embodiments, the thiazide diuretic is hydrochlorothiazide. In some embodiments, the thiazide diuretic is hydroflumethiazide. In some embodiments, the thiazide diuretic is mebutizide. In some embodiments, the thiazide diuretic is methyclothiazide. In some embodiments, the thiazide diuretic is polythiazide. In some embodiments, the thiazide diuretic is trichlormethiazide.

Thiazide-Like Diuretics

As used herein, a thiazide-like diuretic is a sulfonamide diuretic that has similar physiological properties to a thiazide diuretic, but does not have the chemical properties of a thiazide (i.e. does not have the benzothiadiazine core). Examples of thiazide-like diuretics include, but are not limited to, quinethazone, clopamide, chlorthalidone, mefruside, clofenamide, metolazone, meticrane, xipamide, indapamide, clorexolone, and fenquizone.

In some embodiments, the thiazide-like diuretic is quinethazone, clopamide, chlorthalidone, mefruside, clofenamide, metolazone, meticrane, xipamide, indapamide, clorexolone, fenquizone, or the pharmaceutically acceptable salt or hydrate thereof. In some embodiments, the thiazide-like diuretic is quinethazone. In some embodiments, the thiazide-like diuretic is clopamide. In some embodiments, the thiazide-like diuretic is chlorthalidone. In some embodiments, the thiazide-like diuretic is mefruside. In some embodiments, the thiazide-like diuretic is clofenamide. In some embodiments, the thiazide-like diuretic is metolazone. In some embodiments, the thiazide-like diuretic is meticrane. In some embodiments, the thiazide-like diuretic is xipamide. In some embodiments, the thiazide-like diuretic is indapamide or the hydrate thereof. In some embodiments, the thiazide-like diuretic is indapamide. In some embodiments, the thiazide-like diuretic is clorexolone. In some embodiments, the thiazide-like diuretic is fenquizone.

Loop Diuretics

As used herein, loop diuretics are compounds that act on the Na+/K+/2Cl− cotransporter in the thick ascending loop of Henle to inhibit sodium, chloride, and potassium reabsorption. Examples of loop diuretics include, but are not limited to, furosemide, bumetanide, etacrynic acid, etozolin, muzolimine, ozolinone, piretanide, tienilic acid, and torasemide. In some embodiments, the loop diuretic is furosemide, bumetanide, etacrynic acid, etozolin, muzolimine, ozolinone, piretanide, tienilic acid, torasemide, or a pharmaceutically acceptable salt or hydrate thereof.

Other Diuretics

Osmotic diuretics are compounds that cause water to be retained within the proximal tubule and descending limb of loop of Henle. In some embodiments, the osmotic diuretic expands fluid and plasma volume and increases blood flow to the kidney. Examples include, but are not limited to, mannitol and glycerol.

Carbonic Anhydrase Inhibitors

Carbonic anhydrase inhibitors as used herein are compounds that are inhibitors of carbonic anhydrase. In some embodiments, the carbonic anhydrase inhibitor increases the excretion of bicarbonate with accompanying sodium, potassium, and water, which results in an increased flow of alkaline urine. In some embodiments, the carbonic anhydrase inhibitor inhibits the transport of bicarbonate into the interstitium from the proximal convoluted tubule, which leads to less sodium being reabsorbed and provides greater sodium, bicarbonate and water loss in the urine. Examples of such compounds include, but are not limited to, acetazolamide, dichlorphenamide, and methazolamide.

Potassium-Sparing Diuretics

Potassium-sparing diuretics are compounds that either compete with aldosterone for intracellular cytoplasmic receptor sites, or directly block sodium channels, specifically epithelial sodium channels (ENaC). Examples of potassium-sparing diuretics include, but are not limited to, amiloride, spironolactone, eplerenone, triamterene, potassium canrenoate.

Other diuretics contemplated for use also include, but are not limited to, caffeine, theophylline, theobromine, tolvaptan, conivaptan, dopamine, and pamabrom.

In some embodiments, the diuretic is dichlorphenamide, amiloride, pamabrom, mannitol, acetazolamide, methazolamide, spironolactone, triamterene, or the pharmaceutically acceptable salt or hydrate thereof. In some embodiments, the diuretic is dichlorphenamide. In some embodiments, the diuretic is amiloride. In some embodiments, the diuretic is pamabrom. In some embodiments, the diuretic is mannitol. In some embodiments, the diuretic is acetazolamide. In some embodiments, the diuretic is methazolamide. In some embodiments, the diuretic is spironolactone. In some embodiments, the diuretic is triamterene.

Calcium Channel Blockers

As used herein, calcium channel blockers are compounds that promote vasodilator activity by reducing calcium influx into vascular smooth muscle cells. In some embodiments, the calcium channel blocker is amlodipine, nifedipine, diltiazem, nimodipine, verapamil, isradipine, felodipine, nicardipine, nisoldipine, clevidipine, dihydropyridine, lercanidipine, nitrendipine, cilnidipine, manidipine, mibefradil, bepridil, barnidipine, nilvadipine, gallopamil, lidoflazine, aranidipine, dotarizine, diproteverine, or the pharmaceutically acceptable salt or hydrate thereof. In some embodiments, the calcium channel blocker is amlodipine, nifedipine, diltiazem, nimodipine, verapamil, isradipine, felodipine, nicardipine, nisoldipine, clevidipine or the pharmaceutically acceptable salt or hydrate thereof. In some embodiments, the calcium channel blocker is amlodipine or the pharmaceutically acceptable salt thereof. In some embodiments, the calcium channel blocker is amlodipine besylate. In some embodiments, the calcium channel blocker is nifedipine. In some embodiments, the calcium channel blocker is diltiazem. In some embodiments, the calcium channel blocker is nimodipine. In some embodiments, the calcium channel blocker is verapamil. In some embodiments, the calcium channel blocker is isradipine. In some embodiments, the calcium channel blocker is felodipine. In some embodiments, the calcium channel blocker is nicardipine. In some embodiments, the calcium channel blocker is nisoldipine. In some embodiments, the calcium channel blocker is clevidipine.

Lowest Hypertension Therapeutic Dose

As used herein, the lowest hypertension therapeutic dose (LHTD) refers to the lowest strength dose for the single agent for hypertension approved by the US Food and Drug Administration and is not marked as "discontinued" by the Orange Book database (http://www.accessdata.fda.gov/scripts/cder/ob/) as of the filing date of this application. The lowest hypertension therapeutic dose does not include the lowest manufactured dose for cases wherein the lowest hypertension therapeutic dose is not the same as the lowest manufactured dose. Furthermore, the lowest hypertension therapeutic dose does not include the dose as recommended by a physician for cases wherein the lowest hypertension therapeutic dose is not the same dose as recommended by a physician. Further, the lowest hypertension dose of the angiotensin II receptor blocker, diuretic, or calcium channel blocker described herein refers to the dose of the form of angiotensin II receptor blocker, diuretic, or calcium channel blocker approved for use by the US Food and Drug Administration, which includes the free base, pharmaceutically acceptable salt, or hydrate thereof.

In some embodiments, the dose of the angiotensin II receptor blocker is from about 40% to about 80% of the lowest hypertension therapeutic dose. In some embodiments, the dose of the angiotensin II receptor blocker is from about 40% to about 70% of the lowest hypertension therapeutic dose. In some embodiments, the dose of the angiotensin II receptor blocker is from about 40% to about 60% of the lowest hypertension therapeutic dose. In some embodiments, the dose of the angiotensin II receptor blocker is from about 40% to about 50% of the lowest hypertension therapeutic dose. In some embodiments, the dose of the angiotensin II receptor blocker is from about 45% to about 55% of the lowest hypertension therapeutic dose. In some embodiments, the dose of the angiotensin II receptor blocker is from about 50% to about 80% of the lowest hypertension therapeutic dose. In some embodiments, the dose of the angiotensin II receptor blocker is from about 50% to about 70% of the lowest hypertension therapeutic dose. In some embodiments, the dose of the angiotensin II receptor blocker is from about 50% to about 60% of the lowest hypertension therapeutic dose. In some embodiments, the dose of the angiotensin II receptor blocker is from about 60% to about 80% of the lowest hypertension therapeutic dose. In some embodiments, the dose of the angiotensin II receptor blocker is from about 60% to about 70% of the lowest hypertension therapeutic dose. In some embodiments, the dose of the angiotensin II receptor blocker is from about 70% to about 80% of the lowest hypertension therapeutic dose.

In some embodiments, the dose of the angiotensin II receptor blocker is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% of the lowest hypertension therapeutic dose. In some embodiments, the dose of the angiotensin II receptor blocker is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the angiotensin II receptor blocker is about 45%, about 46%, about 47%, about 48%, about 49%, about 50%, about 51%, about 52%, about 53%, about 54%, or about 55% of the lowest hypertension therapeutic dose. In some embodiments, the dose of the angiotensin II receptor blocker is about 50% of the lowest hypertension therapeutic dose. In some embodiments, the dose of the angiotensin II receptor blocker is about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% of the lowest hypertension therapeutic dose. In some embodiments, the dose of the angiotensin II receptor blocker is about 61%, about 62%, about 63%, about 64%, about 65%, about 66%, about 67%, about 68%, about 69%, about 70%, or about 71% of the lowest hypertension therapeutic dose. In some embodiments, the dose of the angiotensin II receptor blocker is about 66% of the lowest hypertension therapeutic dose.

In some embodiments, the dose of the diuretic is from about 40% to about 80% of the lowest hypertension therapeutic dose. In some embodiments, the dose of the diuretic is from about 40% to about 70% of the lowest hypertension therapeutic dose. In some embodiments, the dose of the diuretic is from about 40% to about 60% of the lowest hypertension therapeutic dose. In some embodiments, the dose of the diuretic is from about 40% to about 50% of the lowest hypertension therapeutic dose. In some embodiments, the dose of the diuretic is from about 45% to about 55% of the lowest hypertension therapeutic dose. In some embodiments, the dose of the diuretic is from about 50% to about 80% of the lowest hypertension therapeutic dose. In some embodiments, the dose of the diuretic is from about 50% to about 70% of the lowest hypertension therapeutic dose. In some embodiments, the dose of the diuretic is from about 50% to about 60% of the lowest hypertension therapeutic dose. In some embodiments, the dose of the diuretic is from about 60% to about 80% of the lowest hypertension therapeutic dose. In some embodiments, the dose of the diuretic is from about 60% to about 70% of the lowest hypertension therapeutic dose. In some embodiments, the dose of the diuretic is from about 70% to about 80% of the lowest hypertension therapeutic dose.

In some embodiments, the dose of the diuretic is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% of the lowest hypertension therapeutic dose. In some embodiments, the dose of the diuretic is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the diuretic is about 45%, about 46%, about 47%, about 48%, about 49%, about 50%, about 51%, about 52%, about 53%, about 54%, or about 55% of the lowest hypertension therapeutic dose. In some embodiments, the dose of the diuretic is about 50% of the lowest hypertension therapeutic dose. In some embodiments, the dose of the diuretic is about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% of the lowest hypertension therapeutic dose. In some embodiments, the dose of the diuretic is about 61%, about 62%, about 63%, about 64%, about 65%, about 66%, about 67%, about 68%, about 69%, about 70%, or about 71% of the lowest hypertension therapeutic dose. In some embodiments, the dose of the diuretic is about 66% of the lowest hypertension therapeutic dose.

In some embodiments, the dose of the thiazide diuretic is from about 40% to about 80% of the lowest hypertension therapeutic dose. In some embodiments, the dose of the thiazide diuretic is from about 40% to about 70% of the lowest hypertension therapeutic dose. In some embodiments, the dose of the thiazide diuretic is from about 40% to about 60% of the lowest hypertension therapeutic dose. In some embodiments, the dose of the thiazide diuretic is from about 40% to about 50% of the lowest hypertension therapeutic dose. In some embodiments, the dose of the thiazide diuretic is from about 45% to about 55% of the lowest hypertension therapeutic dose. In some embodiments, the dose of the thiazide diuretic is from about 50% to about 80% of the lowest hypertension therapeutic dose. In some embodiments, the dose of the thiazide diuretic is from about 50% to about 70% of the lowest hypertension therapeutic dose. In some embodiments, the dose of the thiazide diuretic is from about 50% to about 60% of the lowest hypertension therapeutic dose. In some embodiments, the dose of the thiazide diuretic is from about 60% to about 80% of the lowest hypertension therapeutic dose. In some embodiments, the dose of the thiazide diuretic is from about 60% to about 70% of the lowest hypertension therapeutic dose. In some embodiments, the dose of the thiazide diuretic is from about 70% to about 80% of the lowest hypertension therapeutic dose.

In some embodiments, the dose of the thiazide diuretic is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% of the lowest hypertension therapeutic dose. In some embodiments, the dose of the thiazide diuretic is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the thiazide diuretic is about 45%, about 46%, about 47%, about 48%, about 49%, about 50%, about 51%, about 52%, about 53%, about 54%, or about 55% of the lowest hypertension therapeutic dose. In some embodiments, the dose of the thiazide diuretic is about 50% of the lowest hypertension therapeutic dose. In some embodiments, the dose of the thiazide diuretic is about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% of the lowest hypertension therapeutic dose. In some embodiments, the dose of the thiazide diuretic is about 61%, about 62%, about 63%, about 64%, about 65%, about 66%, about 67%, about 68%, about 69%, about 70%, or about 71% of the lowest hypertension therapeutic dose. In some embodiments, the dose of the thiazide diuretic is about 66% of the lowest hypertension therapeutic dose.

In some embodiments, the dose of the thiazide-like diuretic is from about 40% to about 80% of the lowest hypertension therapeutic dose. In some embodiments, the dose of the thiazide-like diuretic is from about 40% to about 70% of the lowest hypertension therapeutic dose. In some embodiments, the dose of the thiazide-like diuretic is from about 40% to about 60% of the lowest hypertension therapeutic dose. In some embodiments, the dose of the thiazide-like diuretic is from about 40% to about 50% of the lowest hypertension therapeutic dose. In some embodiments, the dose of the thiazide-like diuretic is from about 45% to about 55% of the lowest hypertension therapeutic dose. In some embodiments, the dose of the thiazide-like diuretic is from about 50% to about 80% of the lowest hypertension therapeutic dose. In some embodiments, the dose of the thiazide-like diuretic is from about 50% to about 70% of the lowest hypertension therapeutic dose. In some embodiments, the dose of the thiazide-like diuretic is from about 50% to about 60% of the lowest hypertension therapeutic dose. In some embodiments, the dose of the thiazide-like diuretic is from about 60% to about 80% of the lowest hypertension therapeutic dose. In some embodiments, the dose of the thiazide-like diuretic is from about 60% to about 70% of the lowest hypertension therapeutic dose. In some embodiments, the dose of the thiazide-like diuretic is from about 70% to about 80% of the lowest hypertension therapeutic dose.

In some embodiments, the dose of the thiazide-like diuretic is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% of the lowest hypertension therapeutic dose. In some embodiments, the dose of the thiazide-like diuretic is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the thiazide-like diuretic is about 45%, about 46%, about 47%, about 48%, about 49%, about 50%, about 51%, about 52%, about 53%, about 54%, or about 55% of the lowest hypertension therapeutic dose. In some embodiments, the dose of the thiazide-like diuretic is about 50% of the lowest hypertension therapeutic dose. In some embodiments, the dose of the thiazide-like diuretic is about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% of the lowest hypertension therapeutic dose. In some embodiments, the dose of the thiazide-like diuretic is about 61%, about 62%, about 63%, about 64%, about 65%, about 66%, about 67%, about 68%, about 69%, about 70%, or about 71% of the lowest hypertension therapeutic dose. In some embodiments, the dose of the thiazide-like diuretic is about 66% of the lowest hypertension therapeutic dose.

In some embodiments, the dose of the loop diuretic is from about 40% to about 80% of the lowest hypertension therapeutic dose. In some embodiments, the dose of the loop diuretic is from about 40% to about 70% of the lowest hypertension therapeutic dose. In some embodiments, the dose of the loop diuretic is from about 40% to about 60% of the lowest hypertension therapeutic dose. In some embodiments, the dose of the loop diuretic is from about 40% to about 50% of the lowest hypertension therapeutic dose. In some embodiments, the dose of the loop diuretic is from about 45% to about 55% of the lowest hypertension therapeutic dose. In some embodiments, the dose of the loop diuretic is from about 50% to about 80% of the lowest hypertension therapeutic dose. In some embodiments, the dose of the loop diuretic is from about 50% to about 70% of the lowest hypertension therapeutic dose. In some embodiments, the dose of the loop diuretic is from about 50% to about 60% of the lowest hypertension therapeutic dose. In some embodiments, the dose of the loop diuretic is from about 60% to about 80% of the lowest hypertension therapeutic dose. In some embodiments, the dose of the loop diuretic is from about 60% to about 70% of the lowest hypertension therapeutic dose. In some embodiments, the dose of the loop diuretic is from about 70% to about 80% of the lowest hypertension therapeutic dose.

In some embodiments, the dose of the loop diuretic is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% of the lowest hypertension therapeutic dose. In some embodiments, the dose of the loop diuretic is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the loop diuretic is about 45%, about 46%, about 47%, about 48%, about 49%, about 50%, about 51%, about 52%, about 53%, about 54%, or about 55% of the lowest hypertension therapeutic dose. In some embodiments, the dose of the loop diuretic is about 50% of the lowest hypertension therapeutic dose. In some embodiments, the dose of the loop diuretic is about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% of the lowest hypertension therapeutic dose. In some embodiments, the dose of the loop diuretic is about 61%, about 62%, about 63%, about 64%, about 65%, about 66%, about 67%, about 68%, about 69%, about 70%, or about 71% of the lowest hypertension therapeutic dose. In some embodiments, the dose of the loop diuretic is about 66% of the lowest hypertension therapeutic dose.

In some embodiments, the dose of the calcium channel blocker is from about 40% to about 80% of the lowest hypertension therapeutic dose. In some embodiments, the dose of the calcium channel blocker is from about 40% to about 70% of the lowest hypertension therapeutic dose. In some embodiments, the dose of the calcium channel blocker is from about 40% to about 60% of the lowest hypertension therapeutic dose. In some embodiments, the dose of the calcium channel blocker is from about 40% to about 50% of the lowest hypertension therapeutic dose. In some embodiments, the dose of the calcium channel blocker is from about 45% to about 55% of the lowest hypertension therapeutic dose. In some embodiments, the dose of the calcium channel blocker is from about 50% to about 80% of the lowest hypertension therapeutic dose. In some embodiments, the dose of the calcium channel blocker is from about 50% to about 70% of the lowest hypertension therapeutic dose. In some embodiments, the dose of the calcium channel blocker is from about 50% to about 60% of the lowest hypertension therapeutic dose. In some embodiments, the dose of the calcium channel blocker is from about 60% to about 80% of the lowest hypertension therapeutic dose. In some embodiments, the dose of the calcium channel blocker is from about 60% to about 70% of the lowest hypertension therapeutic dose. In some embodiments, the dose of the calcium channel blocker is from about 70% to about 80% of the lowest hypertension therapeutic dose.

In some embodiments, the dose of the calcium channel blocker is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% of the lowest hypertension therapeutic dose. In some embodiments, the dose of the calcium channel blocker is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the calcium channel blocker is about 45%, about 46%, about 47%, about 48%, about 49%, about 50%, about 51%, about 52%, about 53%, about 54%, or about 55% of the lowest hypertension therapeutic dose. In some embodiments, the dose of the calcium channel blocker is about 50% of the lowest hypertension therapeutic dose. In some embodiments, the dose of the calcium channel blocker is about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% of the lowest hypertension therapeutic dose. In some embodiments, the dose of the calcium channel blocker is about 61%, about 62%, about 63%, about 64%, about 65%, about 66%, about 67%, about 68%, about 69%, about 70%, or about 71% of the lowest hypertension therapeutic dose. In some embodiments, the dose of the calcium channel blocker is about 66% of the lowest hypertension therapeutic dose.

In some embodiments, the lowest hypertension therapeutic dose (LHTD) and the corresponding proposed dose and proposed dose range for the following compounds are as described in the following table:

TABLE 1

| Agent | Lowest Hypertension Therapeutic Dose (mg) | Proposed Dose (mg) (% LHTD) | Proposed Dose Range (mg) (% LHTD) |
|---|---|---|---|
| Amlodipine besylate | 2.5 | 1.25 (50% of LHTD) or 1.65 (66% of LHTD) | 1-1.5 (40%-60% of LHTD) or 1.5-2 (60%-80% of LHTD) |
| Chlorthalidone | 25 | 12.5 (50% of LHTD) or 16.5 (66% of LHTD) | 10-15 (40%-60% of LHTD) or 15-20 (60%-80% of LHTD) |
| Hydrochlorothiazide | 12.5 | 6.25 (50% of LHTD) or 8.25 (66% of LHTD) | 5-7.5 (40%-60% of LHTD) or 7.5-10 (60%-80% of LHTD) |
| Indapamide | 1.25 | 0.625 (50% of LHTD) or 0.825 (66% of LHTD) | 0.5-0.75 (40%-60% of LHTD) or 0.75-1.0 (60%-80% of LHTD) |
| Irbesartan | 75 | 37.5 (50% of LHTD) or 49.5 (66% of LHTD) | 30-45 (40%-60% of LHTD) or 45-60 (60%-80% of LHTD) |
| Telmisartan | 20 | 10 (50% of LHTD) or 13.2 (66% of LHTD) | 8-12 (40%-60% of LHTD) or 12-16 (60%-80% of LHTD) |

In some embodiments, the pharmaceutical composition comprises: (a) irbesartan as an angiotensin II receptor blocker; (b) hydrochlorothiazide as a thiazide diuretic; and (c) amlodipine besylate as a calcium channel blocker. In some embodiments, the dose of irbesartan is from about 30 mg to about 45 mg, the dose of hydrochlorothiazide is from about 5 mg to about 7.5 mg, and the dose of amlodipine besylate is from about 1 mg to about 1.5 mg. In some embodiments, the dose of irbesartan is about 37.5 mg, the dose of hydrochlorothiazide is about 6.25 mg, and the dose of amlodipine besylate is about 1.25 mg.

In some embodiments, the pharmaceutical composition comprises: (a) telmisartan as an angiotensin II receptor blocker; (b) hydrochlorothiazide as a thiazide diuretic; and (c) amlodipine besylate as a calcium channel blocker. In some embodiments, the dose of telmisartan is from about 8 mg to about 12 mg, the dose of hydrochlorothiazide is from about 5 mg to about 7.5 mg, and the dose of amlodipine besylate is from about 1 mg to about 1.5 mg. In some embodiments, the dose of telmisartan is about 10 mg, the dose of hydrochlorothiazide is about 6.25 mg, and the dose of amlodipine besylate is about 1.25 mg.

In some embodiments, the pharmaceutical composition comprises: (a) irbesartan as an angiotensin II receptor blocker; (b) indapamide as a thiazide-like diuretic; and (c)

amlodipine besylate as a calcium channel blocker. In some embodiments, the dose of irbesartan is from about 30 mg to about 45 mg, the dose of indapamide is from about 0.5 mg to about 0.75 mg, and the dose of amlodipine besylate is from about 1 mg to about 1.5 mg. In some embodiments, the dose of irbesartan is about 37.5 mg, the dose of indapamide is about 0.625 mg, and the dose of amlodipine besylate is about 1.25 mg.

In some embodiments, the pharmaceutical composition comprises: (a) telmisartan as an angiotensin II receptor blocker; (b) indapamide as a thiazide-like diuretic; (c) amlodipine besylate as a calcium channel blocker. In some embodiments, the dose of telmisartan is from about 8 mg to about 12 mg, the dose of indapamide is from about 0.5 mg to about 0.75 mg, and the dose of amlodipine besylate is from about 1 mg to about 1.5 mg. In some embodiments, dose of telmisartan is about 10 mg, the dose of indapamide is about 0.625 mg, and the dose of amlodipine besylate is about 1.25 mg.

In some embodiments, the pharmaceutical composition comprises: (a) telmisartan as an angiotensin II receptor blocker; (b) chlorthalidone as a thiazide-like diuretic; and (c) amlodipine besylate as a calcium channel blocker. In some embodiments, the dose of telmisartan is from about 8 mg to about 12 mg, the dose of chlorthalidone is from about 10 mg to about 15 mg, and the dose of amlodipine besylate is from about 1 mg to about 1.5 mg. In some embodiments, dose of telmisartan is about 10 mg, the dose of chlorthalidone is about 12.5 mg, and the dose of amlodipine besylate is about 1.25 mg.

In some embodiments, the pharmaceutical composition comprises: (a) irbesartan as an angiotensin II receptor blocker; (b) chlorthalidone as a thiazide-like diuretic; and (c) amlodipine besylate as a calcium channel blocker. In some embodiments, the dose of irbesartan is from about 30 mg to about 45 mg, the dose of chlorthalidone is from about 10 mg to about 15 mg, and the dose of amlodipine besylate is from about 1 mg to about 1.5 mg. In some embodiments, dose of irbesartan is about 37.5 mg, the dose of chlorthalidone is about 12.5 mg, and the dose of amlodipine besylate is about 1.25 mg.

In some embodiments, the pharmaceutical composition comprises: (a) irbesartan as an angiotensin II receptor blocker; (b) hydrochlorothiazide as a thiazide diuretic; and (c) amlodipine besylate as a calcium channel blocker. In some embodiments, the dose of irbesartan is from about 45 mg to about 60 mg, the dose of hydrochlorothiazide is from about 7.5 mg to about 10 mg, and the dose of amlodipine besylate is from about 1.5 mg to about 2 mg. In some embodiments, the dose of irbesartan is about 49.5 mg, the dose of hydrochlorothiazide is about 8.25 mg, and the dose of amlodipine besylate is about 1.65 mg.

In some embodiments, the pharmaceutical composition comprises: (a) telmisartan as an angiotensin II receptor blocker; (b) hydrochlorothiazide as a thiazide diuretic; and (c) amlodipine besylate as a calcium channel blocker. In some embodiments, the dose of telmisartan is from about 12 mg to about 16 mg, the dose of hydrochlorothiazide is from about 7.5 mg to about 10 mg, and the dose of amlodipine besylate is from about 1.5 mg to about 2 mg. In some embodiments, the dose of telmisartan is about 13.2 mg, the dose of hydrochlorothiazide is about 8.25 mg, and the dose of amlodipine besylate is about 1.65 mg.

In some embodiments, the pharmaceutical composition comprises: (a) irbesartan as an angiotensin II receptor blocker; (b) indapamide as a thiazide-like diuretic; and (c) amlodipine besylate as a calcium channel blocker. In some embodiments, the dose of irbesartan is from about 45 mg to about 60 mg, the dose of indapamide is from about 0.75 mg to about 1.0 mg, and the dose of amlodipine besylate is from about 1.5 mg to about 2 mg. In some embodiments, the dose of irbesartan is about 49.5 mg, the dose of indapamide is about 0.825 mg, and the dose of amlodipine besylate is about 1.65 mg.

In some embodiments, the pharmaceutical composition comprises: (a) telmisartan as an angiotensin II receptor blocker; (b) indapamide as a thiazide-like diuretic; (c) amlodipine besylate as a calcium channel blocker. In some embodiments, the dose of telmisartan is from about 12 mg to about 16 mg, the dose of indapamide is from about 0.75 mg to about 1.0 mg, and the dose of amlodipine besylate is from about 1.5 mg to about 2 mg. In some embodiments, dose of telmisartan is about 13.2 mg, the dose of indapamide is about 0.825 mg, and the dose of amlodipine besylate is about 1.65 mg.

In some embodiments, the pharmaceutical composition comprises: (a) telmisartan as an angiotensin II receptor blocker; (b) chlorthalidone as a thiazide-like diuretic; and (c) amlodipine besylate as a calcium channel blocker. In some embodiments, the dose of telmisartan is from about 12 mg to about 16 mg, the dose of chlorthalidone is from about 15 mg to about 20 mg, and the dose of amlodipine besylate is from about 1.5 mg to about 2 mg. In some embodiments, dose of telmisartan is about 13.2 mg, the dose of chlorthalidone is about 16.5 mg, and the dose of amlodipine besylate is about 1.65 mg.

In some embodiments, the pharmaceutical composition comprises: (a) irbesartan as an angiotensin II receptor blocker; (b) chlorthalidone as a thiazide-like diuretic; and (c) amlodipine besylate as a calcium channel blocker. In some embodiments, the dose of irbesartan is from about 45 mg to about 60 mg, the dose of chlorthalidone is from about 15 mg to about 20 mg, and the dose of amlodipine besylate is from about 1.5 mg to about 2 mg. In some embodiments, dose of irbesartan is about 49.5 mg, the dose of chlorthalidone is about 16.5 mg, and the dose of amlodipine besylate is about 1.65 mg.

In some embodiments, the dose of the angiotensin II receptor blocker, such as telmisartan, is from about 80% to about 150% of the lowest hypertension therapeutic dose. In some embodiments, the dose of the angiotensin II receptor blocker is from about 80% to about 140% of the lowest hypertension therapeutic dose. In some embodiments, the dose of the angiotensin II receptor blocker is from about 80% to about 130% of the lowest hypertension therapeutic dose. In some embodiments, the dose of the angiotensin II receptor blocker is from about 80% to about 120% of the lowest hypertension therapeutic dose. In some embodiments, the dose of the angiotensin II receptor blocker is from about 80% to about 110% of the lowest hypertension therapeutic dose.

In some embodiments, the dose of the angiotensin II receptor blocker, such as telmisartan, is from about 85% to about 145% of the lowest hypertension therapeutic dose. In some embodiments, the dose of the angiotensin II receptor blocker is from about 85% to about 135% of the lowest hypertension therapeutic dose. In some embodiments, the dose of the angiotensin II receptor blocker is from about 85% to about 125% of the lowest hypertension therapeutic dose. In some embodiments, the dose of the angiotensin II receptor blocker is from about 85% to about 115% of the lowest hypertension therapeutic dose. In some embodiments, the dose of the angiotensin II receptor blocker is from about 85% to about 105% of the lowest hypertension therapeutic dose.

In some embodiments, the dose of the angiotensin II receptor blocker, such as telmisartan, is from about 90% to about 140% of the lowest hypertension therapeutic dose. In some embodiments, the dose of the angiotensin II receptor blocker is from about 90% to about 130% of the lowest hypertension therapeutic dose. In some embodiments, the dose of the angiotensin II receptor blocker is from about 90% to about 120% of the lowest hypertension therapeutic dose. In some embodiments, the dose of the angiotensin II receptor blocker is from about 90% to about 110% of the lowest hypertension therapeutic dose.

In some embodiments, the dose of the angiotensin II receptor blocker, such as telmisartan, is from about 95% to about 135% of the lowest hypertension therapeutic dose. In some embodiments, the dose of the angiotensin II receptor blocker is from about 95% to about 125% of the lowest hypertension therapeutic dose. In some embodiments, the dose of the angiotensin II receptor blocker is from about 95% to about 115% of the lowest hypertension therapeutic dose. In some embodiments, the dose of the angiotensin II receptor blocker is from about 95% to about 105% of the lowest hypertension therapeutic dose.

In some embodiments, the dose of the angiotensin II receptor blocker is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, about 101%, about 102%, about 103%, about 104%, about 105%, about 106%, about 107%, about 108%, about 109%, about 110%, about 111%, about 112%, about 113%, about 114%, about 115%, about 116%, about 117%, about 118%, about 119%, or about 120% of the lowest hypertension therapeutic dose. In some embodiments, the dose of the angiotensin II receptor blocker is about 90%, about 91%, about 92%, about 93%, about 94%, about 95%, about 96%, about 97%, about 98%, about 99%, about 100%, about 101%, about 102%, about 103%, about 104%, about 105%, about 106%, about 107%, about 108%, about 109%, or about 110% of the lowest hypertension therapeutic dose. In some embodiments, the dose of the angiotensin II receptor blocker is about 95%, about 96%, about 97%, about 98%, about 99%, about 100%, about 101%, about 102%, about 103%, about 104%, or about 105% of the lowest hypertension therapeutic dose. In some embodiments, the dose of the angiotensin II receptor blocker is about 100% of the lowest hypertension therapeutic dose.

In some embodiments, the dose of the thiazide-like diuretic is from about 80% to about 150% of the lowest hypertension therapeutic dose. In some embodiments, the dose of the thiazide-like diuretic is from about 80% to about 140% of the lowest hypertension therapeutic dose. In some embodiments, the dose of the thiazide-like diuretic is from about 80% to about 130% of the lowest hypertension therapeutic dose. In some embodiments, the dose of the thiazide-like diuretic is from about 80% to about 120% of the lowest hypertension therapeutic dose. In some embodiments, the dose of the thiazide-like diuretic is from about 80% to about 110% of the lowest hypertension therapeutic dose.

In some embodiments, the dose of the thiazide-like diuretic is from about 85% to about 145% of the lowest hypertension therapeutic dose. In some embodiments, the dose of the thiazide-like diuretic is from about 85% to about 135% of the lowest hypertension therapeutic dose. In some embodiments, the dose of the thiazide-like diuretic is from about 85% to about 125% of the lowest hypertension therapeutic dose. In some embodiments, the dose of the thiazide-like diuretic is from about 85% to about 115% of the lowest hypertension therapeutic dose. In some embodiments, the dose of the thiazide-like diuretic is from about 85% to about 105% of the lowest hypertension therapeutic dose.

In some embodiments, the dose of the thiazide-like diuretic is from about 90% to about 140% of the lowest hypertension therapeutic dose. In some embodiments, the dose of the thiazide-like diuretic is from about 90% to about 130% of the lowest hypertension therapeutic dose. In some embodiments, the dose of the thiazide-like diuretic is from about 90% to about 120% of the lowest hypertension therapeutic dose. In some embodiments, the dose of the thiazide-like diuretic is from about 90% to about 110% of the lowest hypertension therapeutic dose.

In some embodiments, the dose of the thiazide-like diuretic is from about 95% to about 135% of the lowest hypertension therapeutic dose. In some embodiments, the dose of the thiazide-like diuretic is from about 95% to about 125% of the lowest hypertension therapeutic dose. In some embodiments, the dose of the thiazide-like diuretic is from about 95% to about 115% of the lowest hypertension therapeutic dose. In some embodiments, the dose of the thiazide-like diuretic is from about 95% to about 105% of the lowest hypertension therapeutic dose.

In some embodiments, the dose of the thiazide-like diuretic is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, about 101%, about 102%, about 103%, about 104%, about 105%, about 106%, about 107%, about 108%, about 109%, about 110%, about 111%, about 112%, about 113%, about 114%, about 115%, about 116%, about 117%, about 118%, about 119%, or about 120% of the lowest hypertension therapeutic dose. In some embodiments, the dose of the thiazide-like diuretic is about 90%, about 91%, about 92%, about 93%, about 94%, about 95%, about 96%, about 97%, about 98%, about 99%, about 100%, about 101%, about 102%, about 103%, about 104%, about 105%, about 106%, about 107%, about 108%, about 109%, or about 110% of the lowest hypertension therapeutic dose. In some embodiments, the dose of the thiazide-like diuretic is about 95%, about 96%, about 97%, about 98%, about 99%, about 100%, about 101%, about 102%, about 103%, about 104%, or about 105% of the lowest hypertension therapeutic dose. In some embodiments, the dose of the thiazide-like diuretic blocker is about 100% of the lowest hypertension therapeutic dose.

In some embodiments, the dose of the calcium channel blocker is from about 80% to about 150% of the lowest hypertension therapeutic dose. In some embodiments, the dose of the calcium channel blocker is from about 80% to about 140% of the lowest hypertension therapeutic dose. In some embodiments, the dose of the calcium channel blocker is from about 80% to about 130% of the lowest hypertension therapeutic dose. In some embodiments, the dose of the calcium channel blocker is from about 80% to about 120% of the lowest hypertension therapeutic dose. In some embodiments, the dose of the calcium channel blocker is from about 80% to about 110% of the lowest hypertension therapeutic dose.

In some embodiments, the dose of the calcium channel blocker is from about 85% to about 145% of the lowest hypertension therapeutic dose. In some embodiments, the dose of the calcium channel blocker is from about 85% to about 135% of the lowest hypertension therapeutic dose. In some embodiments, the dose of the calcium channel blocker is from about 85% to about 125% of the lowest hypertension therapeutic dose. In some embodiments, the dose of the calcium channel blocker is from about 85% to about 115% of the lowest hypertension therapeutic dose. In some embodiments, the dose of the calcium channel blocker is from about 85% to about 105% of the lowest hypertension therapeutic dose.

In some embodiments, the dose of the calcium channel blocker is from about 90% to about 140% of the lowest hypertension therapeutic dose. In some embodiments, the dose of the calcium channel blocker is from about 90% to about 130% of the lowest hypertension therapeutic dose. In some embodiments, the dose of the calcium channel blocker is from about 90% to about 120% of the lowest hypertension therapeutic dose. In some embodiments, the dose of the calcium channel blocker is from about 90% to about 110% of the lowest hypertension therapeutic dose.

In some embodiments, the dose of the calcium channel blocker is from about 95% to about 135% of the lowest hypertension therapeutic dose. In some embodiments, the dose of the calcium channel blocker is from about 95% to about 125% of the lowest hypertension therapeutic dose. In some embodiments, the dose of the calcium channel blocker is from about 95% to about 115% of the lowest hypertension therapeutic dose. In some embodiments, the dose of the calcium channel blocker is from about 95% to about 105% of the lowest hypertension therapeutic dose.

In some embodiments, the dose of the calcium channel blocker is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, about 101%, about 102%, about 103%, about 104%, about 105%, about 106%, about 107%, about 108%, about 109%, about 110%, about 111%, about 112%, about 113%, about 114%, about 115%, about 116%, about 117%, about 118%, about 119%, or about 120% of the lowest hypertension therapeutic dose. In some embodiments, the dose of the calcium channel blocker is about 90%, about 91%, about 92%, about 93%, about 94%, about 95%, about 96%, about 97%, about 98%, about 99%, about 100%, about 101%, about 102%, about 103%, about 104%, about 105%, about 106%, about 107%, about 108%, about 109%, or about 110% of the lowest hypertension therapeutic dose. In some embodiments, the dose of the calcium channel blocker is about 95%, about 96%, about 97%, about 98%, about 99%, about 100%, about 101%, about 102%, about 103%, about 104%, or about 105% of the lowest hypertension therapeutic dose. In some embodiments, the dose of the calcium channel blocker is about 100% of the lowest hypertension therapeutic dose.

In some embodiments, the lowest hypertension therapeutic dose (LHTD) and the corresponding proposed dose and proposed dose range for the following compounds are as described in the following table:

TABLE 2

| Agent | Lowest Hypertension Therapeutic Dose (mg) | Proposed Dose (mg) (% LHTD) | Proposed Dose Range (mg) (% LHTD) |
| --- | --- | --- | --- |
| Amlodipine besylate | 2.5 | 2.5 (100% of LHTD) or 5 (200% of LHTD) | 2-3.75 (80%-150% of LHTD); 2-3 (80%-120% of LHTD); 2.25-2.75 (90%-110% of LHTD); or 3.75-6.25 (150%-250% of LHTD) |
| Chlorthalidone | 25 | 25 (100% of LHTD) or 50 (200% of LHTD) | 20-37.5 (80%-150% of LHTD); 20-30 (80%-120% of LHTD); 22.5-27.5 (90%-110% of LHTD); or 37.5-62.5 (150%-250% of LHTD) |
| Hydrochlorothiazide | 12.5 | 12.5 (100% of LHTD) or 25 (200% of LHTD) | 10-18.75 (80%-150% of LHTD); 10-15 (80%-120%) of LHTD); 11.25-13.75 (90%-110% of LHTD); or 18.75-31.25 (150%-250% of LHTD) |
| Indapamide | 1.25 | 1.25 (100% of LHTD) or 2.5 (200% of LHTD) | 1-1.875 (80%-150% of LHTD); 1-1.5 (80%-120% of LHTD); 1.125-1.375 (90%-110% of LHTD); or 1.875-3.125 (150%-250% of LHTD) |
| Irbesartan | 75 | 75 (100% of LHTD) or 150 (200% of LHTD) | 60-112.5 (80%-150% of LHTD); 60-90 (80%-120% of LHTD); 67.5-82.5 (90%-110% of LHTD); or 112.5-187.5 (150%-250% of LHTD) |
| Telmisartan | 20 | 20 (100% of LHTD) or 40 (200% of LHTD) | 16-30 (80%-150% of LHTD); 16-24 (80%-120% of LHTD); 18-22 (90%-110% of LHTD); or 30-50 (150%-250% of LHTD) |

In some embodiments, the dose of any one of the angiotensin II receptor blocker, the diuretic, and the calcium channel blocker is substituted with from about 80% to about 250% of the lowest hypertension therapeutic dose (LHTD) for the angiotensin II receptor blocker, the diuretic, or the calcium channel blocker. In some embodiments, the dose of the angiotensin II receptor blocker is substituted with from about 80% to about 250% of the lowest hypertension therapeutic dose (LHTD) for the angiotensin II receptor blocker. In some embodiments, the dose of the diuretic is substituted with from about 80% to about 250% of the lowest hypertension therapeutic dose (LHTD) for the diuretic. In some embodiments, the dose of the calcium channel blocker is substituted with from about 80% to about 250% of the lowest hypertension therapeutic dose (LHTD) for the calcium channel blocker. In some embodiments, the dose of any one of the angiotensin II receptor blocker, the diuretic, and the calcium channel blocker is substituted with from about 80% to about 150% of the lowest hypertension therapeutic dose (LHTD) for the angiotensin II receptor blocker, the diuretic, or the calcium channel blocker. In some embodiments, the dose of the angiotensin II receptor blocker is substituted with from about 80% to about 150% of the lowest hypertension therapeutic dose (LHTD) for the angiotensin II receptor blocker. In some embodiments, the dose of the angiotensin II receptor blocker is substituted with about 100% of the lowest hypertension therapeutic dose (LHTD) for the angiotensin II receptor blocker. In some embodiments, the dose of the diuretic is substituted with from about 80% to about 150% of the lowest hypertension therapeutic dose (LHTD) for the diuretic. In some embodiments, the dose of the diuretic is substituted with about 100% of the lowest hypertension therapeutic dose (LHTD) for the diuretic. In some embodiments, the dose of the calcium channel blocker is substituted with from about 80% to about 150% of the lowest hypertension therapeutic dose (LHTD) for the calcium channel blocker. In some embodiments, the dose of the calcium channel blocker is substituted with about 100% of the lowest hypertension therapeutic dose (LHTD) for the calcium channel blocker. In some embodiments, the dose of any one of the angiotensin II receptor blocker, the diuretic, and the calcium channel blocker is substituted with from about 150% to about 250% of the lowest hypertension therapeutic dose (LHTD) for the angiotensin II receptor blocker, the diuretic, or the calcium channel blocker. In some embodiments, the dose of the angiotensin II receptor blocker is substituted with from about 150% to about 250% of the lowest hypertension therapeutic dose (LHTD) for the angiotensin II receptor blocker. In some embodiments, the dose of the angiotensin II receptor blocker is substituted with about 200% of the lowest hypertension therapeutic dose (LHTD) for the angiotensin II receptor blocker. In some embodiments, the dose of the diuretic is substituted with from about 150% to about 250% of the lowest hypertension therapeutic dose (LHTD) for the diuretic. In some embodiments, the dose of the diuretic is substituted with about 200% of the lowest hypertension therapeutic dose (LHTD) for the diuretic. In some embodiments, the dose of the calcium channel blocker is substituted with from about 150% to about 250% of the lowest hypertension therapeutic dose (LHTD) for the calcium channel blocker. In some embodiments, the dose of the calcium channel blocker is substituted with about 200% of the lowest hypertension therapeutic dose (LHTD) for the calcium channel blocker.

In some embodiments, the dose of any two of the angiotensin II receptor blocker, the diuretic, and the calcium channel blocker is substituted with from about 80% to about 250% of the lowest hypertension therapeutic dose (LHTD) for the angiotensin II receptor blocker, the diuretic, or the calcium channel blocker. In some embodiments, the dose of the angiotensin II receptor blocker is substituted with from about 80% to about 250% of the lowest hypertension therapeutic dose (LHTD) for the angiotensin II receptor blocker. In some embodiments, the dose of the diuretic is substituted with from about 80% to about 250% of the lowest hypertension therapeutic dose (LHTD) for the diuretic. In some embodiments, the dose of the calcium channel blocker is substituted with from about 80% to about 250% of the lowest hypertension therapeutic dose (LHTD) for the calcium channel blocker. In some embodiments, the dose of any two of the angiotensin II receptor blocker, the diuretic, and the calcium channel blocker is substituted with from about 80% to about 150% of the lowest hypertension therapeutic dose (LHTD) for the angiotensin II receptor blocker, the diuretic, or the calcium channel blocker. In some embodiments, the dose of the angiotensin II receptor blocker is substituted with from about 80% to about 150% of the lowest hypertension therapeutic dose (LHTD) for the angiotensin II receptor blocker. In some embodiments, the dose of the angiotensin II receptor blocker is substituted with about 100% of the lowest hypertension therapeutic dose (LHTD) for the angiotensin II receptor blocker. In some embodiments, the dose of the diuretic is substituted with from about 80% to about 150% of the lowest hypertension therapeutic dose (LHTD) for the diuretic. In some embodiments, the dose of the diuretic is substituted with about 100% of the lowest hypertension therapeutic dose (LHTD) for the diuretic. In some embodiments, the dose of the calcium channel blocker is substituted with from about 80% to about 150% of the lowest hypertension therapeutic dose (LHTD) for the calcium channel blocker. In some embodiments, the dose of the calcium channel blocker is substituted with about 100% of the lowest hypertension therapeutic dose (LHTD) for the calcium channel blocker. In some embodiments, the dose of any two of the angiotensin II receptor blocker, the diuretic, and the calcium channel blocker is substituted with from about 150% to about 250% of the lowest hypertension therapeutic dose (LHTD) for the angiotensin II receptor blocker, the diuretic, or the calcium channel blocker. In some embodiments, the dose of the angiotensin II receptor blocker is substituted with from about 150% to about 250% of the lowest hypertension therapeutic dose (LHTD) for the angiotensin II receptor blocker. In some embodiments, the dose of the angiotensin II receptor blocker is substituted with about 200% of the lowest hypertension therapeutic dose (LHTD) for the angiotensin II receptor blocker. In some embodiments, the dose of the diuretic is substituted with from about 150% to about 250% of the lowest hypertension therapeutic dose (LHTD) for the diuretic. In some embodiments, the dose of the diuretic is substituted with about 200% of the lowest hypertension therapeutic dose (LHTD) for the diuretic. In some embodiments, the dose of the calcium channel blocker is substituted with from about 150% to about 250% of the lowest hypertension therapeutic dose (LHTD) for the calcium channel blocker. In some embodiments, the dose of the calcium channel blocker is substituted with about 200% of the lowest hypertension therapeutic dose (LHTD) for the calcium channel blocker.

In some embodiments, the dose of the angiotensin II receptor blocker, the diuretic (e.g., a thiazide diuretic or thiazide-like diuretic), and the calcium channel blocker are each independently from about 80% to about 150% of the lowest hypertension therapeutic dose (LHTD) for the angiotensin II receptor blocker, the diuretic, or the calcium channel blocker. In some embodiments, the dose of the angiotensin II receptor blocker is from about 80% to about 150% of the lowest hypertension therapeutic dose (LHTD) for the angiotensin II receptor blocker. In some embodiments, the dose of the diuretic is from about 80% to about 150% of the lowest hypertension therapeutic dose (LHTD) for the diuretic. In some embodiments, the dose of the calcium channel blocker is from about 80% to about 150% of the lowest hypertension therapeutic dose (LHTD) for the calcium channel blocker. In some embodiments, the dose of the angiotensin II receptor blocker, the diuretic, and the calcium channel blocker are each independently from about 80% to about 120% of the lowest hypertension therapeutic dose (LHTD) for the angiotensin II receptor blocker, the diuretic, or the calcium channel blocker. In some embodiments, the dose of the angiotensin II receptor blocker is from about 80% to about 120% of the lowest hypertension therapeutic dose (LHTD) for the angiotensin II receptor blocker. In some embodiments, the dose of the angiotensin II receptor blocker is about 100% of the lowest hypertension therapeutic dose (LHTD) for the angiotensin II receptor blocker. In some embodiments, the dose of the diuretic is from about 80% to about 120% of the lowest hypertension therapeutic dose (LHTD) for the diuretic. In some embodiments, the dose of the diuretic is about 100% of the lowest hypertension therapeutic dose (LHTD) for the diuretic. In some embodiments, the dose of the calcium channel blocker is from about 80% to about 120% of the lowest hypertension therapeutic dose (LHTD) for the calcium channel blocker. In some embodiments, the dose of the calcium channel blocker is about 100% of the lowest hypertension therapeutic dose (LHTD) for the calcium channel blocker. In some embodiments, the dose of the angiotensin II receptor blocker, the diuretic, and the calcium channel blocker are each independently from about 90% to about 110% of the lowest hypertension therapeutic dose (LHTD) for the angiotensin II receptor blocker, the diuretic, or the calcium channel blocker. In some embodiments, the dose of the angiotensin II receptor blocker is from about 90% to about 110% of the lowest hypertension therapeutic dose (LHTD) for the angiotensin II receptor blocker. In some embodiments, the dose of the angiotensin II receptor blocker is about 100% of the lowest hypertension therapeutic dose (LHTD) for the angiotensin II receptor blocker. In some embodiments, the dose of the diuretic is about 90% to about 110% of the lowest hypertension therapeutic dose (LHTD) for the diuretic. In some embodiments, the dose of the diuretic is about 100% of the lowest hypertension therapeutic dose (LHTD) for the diuretic. In some embodiments, the dose of the calcium channel blocker is from about 90% to about 110% of the lowest hypertension therapeutic dose (LHTD) for the calcium channel blocker. In some embodiments, the dose of the calcium channel blocker is about 100% of the lowest hypertension therapeutic dose (LHTD) for the calcium channel blocker.

In some embodiments, the pharmaceutical composition comprises: (a) telmisartan as an angiotensin II receptor blocker; (b) indapamide as a thiazide-like diuretic; (c) amlodipine besylate as a calcium channel blocker. In some embodiments, the dose of telmisartan is from about 16 mg to about 30 mg, the dose of indapamide is from about 1 mg to about 1.875 mg, and the dose of amlodipine besylate is from about 2 mg to about 3.75 mg.

In some embodiments, the dose of telmisartan is from about 16 mg to about 24 mg, the dose of indapamide is from about 1 mg to about 1.5 mg, and the dose of amlodipine besylate is from about 2 mg to about 3 mg.

In some embodiments, the dose of telmisartan is from about 18 mg to about 22 mg, the dose of indapamide is from about 1.125 mg to about 1.375 mg, and the dose of amlodipine besylate is from about 2.25 mg to about 2.75 mg.

In some embodiments, dose of telmisartan is about 20 mg, the dose of indapamide is about 1.25 mg, and the dose of amlodipine besylate is about 2.5 mg.

In some embodiments, the pharmaceutical composition comprises: (a) telmisartan as an angiotensin II receptor blocker; (b) chlorthalidone as a thiazide-like diuretic; and (c) amlodipine besylate as a calcium channel blocker. In some embodiments, the dose of telmisartan is from about 16 mg to about 30 mg, the dose of chlorthalidone is from about 20 mg to about 37.5 mg, and the dose of amlodipine besylate is from about 2 mg to about 3.75 mg.

In some embodiments, the dose of telmisartan is from about 16 mg to about 24 mg, the dose of chlorthalidone is from about 20 mg to about 30 mg, and the dose of amlodipine besylate is from about 2 mg to about 3 mg.

In some embodiments, the dose of telmisartan is from about 18 mg to about 22 mg, the dose of chlorthalidone is from about 22.5 mg to about 27.5 mg, and the dose of amlodipine besylate is from about 2.25 mg to about 2.75 mg.

In some embodiments, dose of telmisartan is about 20 mg, the dose of chlorthalidone is about 25 mg, and the dose of amlodipine besylate is about 2.5 mg.

Formulations

In some embodiments, the angiotensin II receptor blocker, the diuretic, and the calcium channel blocker are provided in one formulation. In some embodiments, the angiotensin II receptor blocker, the diuretic, and the calcium channel blocker each provided in a separate formulation. In some embodiments, two of the angiotensin II receptor blocker, the diuretic, and the calcium channel blocker are provided in one formulation. In some embodiments, the angiotensin II receptor and the diuretic are provided in one formulation. In some embodiments, the angiotensin II receptor blocker and the calcium channel blocker are provided in one formulation. In some embodiments, the diuretic and the calcium channel blocker are provided in one formulation. In some embodiments, the angiotensin II receptor blocker, the diuretic, and the calcium channel blocker are provided in one formulation. In some embodiments, the pharmaceutical composition is in the form of pill, tablet, or capsule. In some embodiments, the pharmaceutical composition is in the form of pill. In some embodiments, the pharmaceutical composition is in the form of tablet. In some embodiments, the pharmaceutical composition is in the form of capsule. In some embodiments, the pharmaceutical composition is suitable for oral administration.

Other suitable formulations include, but are not limited to, those suitable for rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose.

Exemplary pharmaceutical compositions may be used in the form of a pharmaceutical preparation, for example, in solid, semisolid, or liquid form, which includes one or more of a disclosed compound, as an active ingredient, in admixture with an organic or inorganic carrier or excipient suitable for external, enteral, or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills, and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. In some embodiments, capsules are prepared by encapsulating tablets in hard-gelatin capsules (e.g. overencapsulation.) Tablets, and other solid dosage forms, such as dragees, capsules, pills and granules, may optionally be scored or prepared with coatings and shells, such as enteric coatings and other coatings well known in the pharmaceutical-formulating art.

In some embodiments, the angiotensin II receptor blockers of the pharmaceutical compositions described herein can be replaced with angiotensin converting enzyme inhibitors (ACE inhibitors). Examples of suitable angiotensin converting enzyme inhibitors include, but are not limited to, benazepril, captopril, enalapril, fosinopril, lisinopril, moexipril, perindopril, quinapril, ramipril, trandolapril or the pharmaceutically acceptable salt or hydrate thereof. In some embodiments, the dose of the angiotensin-converting enzyme inhibitor is from about 80% to about 150% of the lowest hypertension therapeutic dose. In some embodiments, the dose of the angiotensin-converting enzyme inhibitor is from about 80% to about 120% of the lowest hypertension therapeutic dose. In some embodiments, the dose of the angiotensin-converting enzyme inhibitor is from about 90% to about 110% of the lowest hypertension therapeutic dose. In some embodiments, the dose of the angiotensin-converting enzyme inhibitor is about 100% of the lowest hypertension therapeutic dose. In some embodiments, the dose of the angiotensin-converting enzyme inhibitor is from about 40% to about 80% of the lowest hypertension therapeutic dose. In some embodiments, the dose of the angiotensin-converting enzyme inhibitor is from about 40% to about 70% of the lowest hypertension therapeutic dose. In some embodiments, the dose of the angiotensin-converting enzyme inhibitor is from about 40% to about 60% of the lowest hypertension therapeutic dose. In some embodiments, the dose of the angiotensin-converting enzyme inhibitor is from about 40% to about 50% of the lowest hypertension therapeutic dose. In some embodiments, the dose of the angiotensin-converting enzyme inhibitor is from about 45% to about 55% of the lowest hypertension therapeutic dose. In some embodiments, the dose of the angiotensin-converting enzyme inhibitor is from about 50% to about 80% of the lowest hypertension therapeutic dose. In some embodiments, the dose of the angiotensin-converting enzyme inhibitor is from about 50% to about 70% of the lowest hypertension therapeutic dose. In some embodiments, the dose of the angiotensin-converting enzyme inhibitor is from about 50% to about 60% of the lowest hypertension therapeutic dose. In some embodiments, the dose of the angiotensin-converting enzyme inhibitor is from about 60% to about 80% of the lowest hypertension therapeutic dose. In some embodiments, the dose of the angiotensin-converting enzyme inhibitor is from about 60% to about 70% of the lowest hypertension therapeutic dose. In some embodiments, the dose of the angiotensin-converting enzyme inhibitor is from about 70% to about 80% of the lowest hypertension therapeutic dose. In some embodiments, the dose of the angiotensin-converting enzyme inhibitor is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% of the lowest hypertension therapeutic dose. In some embodiments, the dose of the angiotensin-converting enzyme inhibitor is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the lowest hypertension therapeutic dose. In some embodiments, the dose of the angiotensin-converting enzyme inhibitor is about 45%, about 46%, about 47%, about 48%, about 49%, about 50%, about 51%, about 52%, about 53%, about 54%, or about 55% of the lowest hypertension therapeutic dose. In some embodiments, the dose of the angiotensin-converting enzyme inhibitor is about 50% of the lowest hypertension therapeutic dose. In some embodiments, the dose of the angiotensin-converting enzyme inhibitor is about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% of the lowest hypertension therapeutic dose. In some embodiments, the dose of the angiotensin-converting enzyme inhibitor is about 61%, about 62%, about 63%, about 64%, about 65%, about 66%, about 67%, about 68%, about 69%, about 70%, or about 71% of the lowest hypertension therapeutic dose. In some embodiments, the dose of the angiotensin-converting enzyme inhibitor is about 66% of the lowest hypertension therapeutic dose.

Methods of Treatment

The pharmaceutical compositions described herein are useful for treating hypertension in a subject in need thereof. In some embodiments, the treatment results in a systolic blood pressure (SBP) of less than about 140 mmHg. In some embodiments, the treatment results in a systolic blood pressure (SBP) of less than about 135 mmHg. In some embodiments, the treatment results in a reduction of systolic blood pressure (SBP) of about 10 mmHg or greater. In some embodiments, the treatment results in a reduction of systolic blood pressure (SBP) of about 10 mmHg to about 20 mmHg. In some embodiments, the treatment results in a reduction of systolic blood pressure (SBP) of about 10 mmHg to about 30 mmHg. In some embodiments, the treatment results in a reduction of systolic blood pressure (SBP) of about 10 mmHg, about 11 mmHg, about 12 mmHg, about 13 mmHg, about 14 mmHg, about 15 mmHg, about 16 mmHg, about 17 mmHg, about 18 mmHg, about 19 mmHg, or about 20 mmHg. In some embodiments, the treatment results in a reduction of systolic blood pressure (SBP) of about 10 mmHg, about 11 mmHg, about 12 mmHg, about 13 mmHg, about 14 mmHg, about 15 mmHg, about 16 mmHg, about 17 mmHg, about 18 mmHg, about 19 mmHg, about 20 mmHg, about 21 mmHg, about 22 mmHg, about 23 mmHg, about 24 mmHg, about 25 mmHg, about 26 mmHg, about 27 mmHg, about 28 mmHg, about 29 mmHg, or about 30 mmHg. In some embodiments, the treatment results in a diastolic blood pressure (DBP) of less than about 90 mmHg. In some embodiments, the treatment results in a diastolic blood pressure (DBP) of less than about 85 mmHg. In some embodiments, treatment results in a reduction of diastolic blood pressure (DBP) of about 5 mmHg or greater. In some embodiments, treatment results in a reduction of diastolic blood pressure (DBP) of about 5 mmHg to about 10 mmHg. In some embodiments, treatment results in a reduction of diastolic blood pressure (DBP) of about 5 mmHg to about 15 mmHg. In some embodiments, treatment results in a reduction of diastolic blood pressure (DBP) of about 5 mmHg, about 6 mmHg, about 7 mmHg, about 8 mmHg, about 9 mmHg, or about 10 mmHg. In some embodiments, treatment results in a reduction of diastolic blood pressure (DBP) of about 5 mmHg, about 6 mmHg, about 7 mmHg, about 8 mmHg, about 9 mmHg, about 10 mmHg, about 11 mmHg, about 12 mmHg, about 13 mmHg, about 14 mmHg, or about 15 mmHg.

In some embodiments, treatment results in a reduction in systolic blood pressure (SBP) that is greater than the reduction obtained with the full lowest hypertension therapeutic dose of any one of the angiotensin II receptor blocker, the diuretic, and the calcium channel blocker in the pharmaceutical composition. In some embodiments, treatment results in a reduction in systolic blood pressure (SBP) that is greater than the reduction obtained with the full lowest hypertension therapeutic dose of the angiotensin II receptor blocker in the pharmaceutical composition. In some embodiments, treatment results in a reduction in systolic blood pressure (SBP) that is greater than the reduction obtained with the full lowest hypertension therapeutic dose of the diuretic in the pharmaceutical composition. In some embodiments, treatment results in a reduction in systolic blood pressure (SBP) that is greater than the reduction obtained with the full lowest hypertension therapeutic dose of the calcium channel blocker in the pharmaceutical composition.

In some embodiments, treatment results in a reduction in diastolic blood pressure (DBP) that is greater than the reduction obtained with the full lowest hypertension therapeutic dose of any one of the angiotensin II receptor blocker, the diuretic, and the calcium channel blocker in the pharmaceutical composition. In some embodiments, treatment results in a reduction in diastolic blood pressure (DBP) that is greater than the reduction obtained with the full lowest hypertension therapeutic dose of the angiotensin II receptor blocker in the pharmaceutical composition. In some embodiments, treatment results in a reduction in diastolic blood pressure (DBP) that is greater than the reduction obtained with the full lowest hypertension therapeutic dose of the diuretic in the pharmaceutical composition. In some embodiments, treatment results in a reduction in diastolic blood pressure (DBP) that is greater than the reduction obtained with the full lowest hypertension therapeutic dose of the calcium channel blocker in the pharmaceutical composition.

In some embodiments, treatment results in greater long term tolerability and reduced risk of side effects when compared to treatment with the full lowest hypertension therapeutic dose of any one of the angiotensin II receptor blocker, the diuretic, and the calcium channel blocker in the pharmaceutical composition. In some embodiments, the treatment results in greater long term tolerability and reduced risk of side effects when compared to treatment with the full lowest hypertension therapeutic dose of the angiotensin II receptor blocker in the pharmaceutical composition. In some embodiments, the treatment results in greater long term tolerability and reduced risk of side effects when compared to treatment with the full lowest hypertension therapeutic dose of the diuretic in the pharmaceutical composition. In some embodiments, the treatment results in greater long term tolerability and reduced risk of side effects when compared to treatment with the full lowest hypertension therapeutic dose of the calcium channel blocker in the pharmaceutical composition.

In some embodiments, treatment results in a reduction in systolic blood pressure (SBP) that is greater than or equal to the reduction obtained with the combination of any two of the angiotensin II receptor blocker, the diuretic, and the calcium channel blocker in the pharmaceutical composition, wherein the dose of each angiotensin II receptor blocker, the diuretic, and the calcium channel blocker is about 50% of the lowest hypertension therapeutic dose. In some embodiments, treatment results in a reduction in diastolic blood pressure (DBP) that is greater than or equal to the reduction obtained with a combination of any two of the angiotensin II receptor blocker, the diuretic, and the calcium channel blocker in the pharmaceutical composition, wherein the dose of each the angiotensin II receptor blocker, the diuretic, and the calcium channel blocker is about 50% of the lowest hypertension therapeutic dose. In some embodiments, the treatment results in greater long term tolerability and reduced risk of side effects when compared to treatment with a combination of any two of the angiotensin II receptor blocker, the diuretic, and the calcium channel blocker in the pharmaceutical composition, wherein the dose of each the angiotensin II receptor blocker, the diuretic, and the calcium channel blocker is about 50% of the lowest hypertension therapeutic dose.

In some embodiments, the treatment is the initial or first-line treatment of hypertension. In some embodiments, the subject has a very mild elevation of blood pressure prior to treatment. In some embodiments, the subject is not on any previous hypertension therapy prior to treatment. In some embodiments, the subject has a very mild elevation of blood pressure prior to treatment and is not on any previous hypertension therapy prior to treatment.

This present disclosure recognizes that the use of the angiotensin II receptor blocker in the pharmaceutical compositions disclosed herein in some embodiments provides beneficial therapeutic effects, which include, but are not limited to, significant reduction in blood pressure, significant reduction in blood pressure among subjects with mild elevation in blood pressure, greater long term tolerability, and reduced risk of side effects. This present disclosure recognizes that the exclusion of a lipid-regulating agent, a platelet function-altering agent, a serum homocysteine-lowering agent, or a combination thereof in the pharmaceutical compositions disclosed herein in some embodiments provides beneficial therapeutic effects, which include, but are not limited to, significant reduction in blood pressure, significant reduction in blood pressure among subjects with mild elevation in blood pressure, greater long term tolerability, and reduced risk of side effects.

It is also recognized herein that in some embodiments, the triple combination described herein comprising an angiotensin II receptor blocker, a diuretic, and a calcium channel blocker with each component at about 40% to about 80% of the lowest hypertension therapeutic dose provide significantly larger reductions in blood pressure (such as systolic blood pressure, diastolic blood pressure, or both) than a triple combination comprising angiotensin II receptor blocker (such as losartan), a diuretic (such as hydrochlorothiazide), and a calcium channel blocker (amlodipine besylate) with each component at 100% of the lowest hypertension therapeutic dose. In some embodiments, the triple combination described herein comprising an angiotensin II receptor blocker, a diuretic, and a calcium channel blocker with each component at about 40% to about 60% of the lowest hypertension therapeutic dose provide significantly larger reductions in blood pressure (such as systolic blood pressure, diastolic blood pressure, or both) than a triple combination comprising angiotensin II receptor blocker (such as losartan), a diuretic (such as hydrochlorothiazide), and a calcium channel blocker (amlodipine besylate) with each component at 100% of the lowest hypertension therapeutic dose.

It is also recognized herein that in some embodiments, the triple combination described herein comprising telmisartan, a thiazide-like diuretic, and a calcium channel blocker with each component at about 80% to about 150% of the lowest hypertension therapeutic dose provide significantly larger reductions in blood pressure (such as systolic blood pressure, diastolic blood pressure, or both) than a triple combination comprising losartan as angiotensin II receptor blocker, a thiazide diuretic (such as hydrochlorothiazide), and a calcium channel blocker (amlodipine besylate). In some embodiments, the triple combination described herein comprising telmisartan, a thiazide-like diuretic, and a calcium channel blocker with each component at about 80% to about 120% of the lowest hypertension therapeutic dose provide significantly larger reductions in blood pressure (such as systolic blood pressure, diastolic blood pressure, or both) than a triple combination comprising losartan as angiotensin II receptor blocker, a thiazide diuretic (such as hydrochlorothiazide), and a calcium channel blocker (amlodipine besylate).

EXAMPLES

Example 1: Cardiovascular Measurement in Spontaneously Hypertensive Rats Receiving Combinations of Anti-Hypertensive Drugs Summary The purpose of this study was to evaluate the comparative effects on blood pressure of three different combinations of an angiotensin II receptor blocker, a calcium channel blocker, and a diuretic (a thiazide diuretic or a thiazide-like diuretic). The main objectives were to assess whether there were differences in the effects of combinations utilizing different drugs from the same class, and differences between combinations utilizing the same drugs at different doses, including very low doses (i.e., doses below the lowest doses approved and manufactured, such as those at 50% of the lowest hypertension therapeutic dose (LHTD)).

The specific combinations studied were:
Combination 1: telmisartan, amlodipine besylate, and indapamide, all at 50% of the lowest hypertension therapeutic dose (LHTD) or one-quarter of the FDA recommended usual maintenance dose (corresponds to telmisartan 10 mg, amlodipine besylate 1.25 mg, and indapamide 0.625 mg);
Combination 2: telmisartan, amlodipine, and indapamide, all at 100% of the lowest hypertension therapeutic dose (LHTD) or one-half of the FDA recommended usual maintenance dose (corresponds to telmisartan 20 mg, amlodipine besylate 2.5 mg, and indapamide 1.25 mg); and
Combination 3: losartan, amlodipine besylate, and hydrochlorothiazide, all at 100% of the lowest hypertension therapeutic dose (LHTD) or one-half of the FDA recommended usual maintenance dose (corresponds to losartan 25 mg, amlodipine besylate 2.5 mg, and hydrochlorothiazide 12.5 mg).

The study was conducted in spontaneously hypertensive rats (SHR), the most commonly-used animal model for the study of hypertension (See: Pinto Y M, Paul M, Ganten D. "Lessons from rat models of hypertension: from Goldblatt to genetic engineering". *Cardiovascular Research*. 39 (1): 77-88.). Drug doses were calculated using standard allometric scaling methods and data from the published literature on $C_{max}$ and AUC for each of the six antihypertensive agents. Each animal was exposed to a single dose of every drug combination in a Latin square design.

Methods

The following was used as the vehicle for the following study: 0.5% methylcellulose (w/v) and 0.25% polysorbate 80 (v/v) in 25 mM phosphate buffer at pH 8+/−0.2.

The following animals were used in the study: Spontaneous Hypertensive rats (Strain: SHR/NCrl). The rats were obtained from Charles River Laboratories, Inc., Kingston, New York. The age at initiation of dosing was at approximately 12 weeks. 13 male rats were used for acclimation. 8 male rats were used for the study. The animals were identified by cage card and tattoo.

Telemetry Implantation: The animals were implanted with Data Science International transmitters (HD-S10) for collection for blood pressure and heart rate data. The animals were not administered dose formulations until at least 10 days after surgery.

Housing: The animals were individually housed in solid bottom cages equipped with water bottles.

Diet: Teklad Global Diet—Rodent 2014 (Envigo RMS, Inc.) were provided ad libitum unless otherwise specified. In some instances, the animals were fed the meal-form of this diet if indicated by health conditions.

Water: Greenfield city water was provided ad libitum.

Contaminants: No known contaminants were present in the diet, water, or bedding (if applicable) at levels that would interfere with this study.

Environment: Environmental controls for the animal room were set to maintain the following room conditions: a temperature range of 20 to 26° C., a relative humidity of 30 to 70%, and a 12-hour light/12-hour dark cycle.

Acclimation (Pre-dose Phase): The acclimation phase was for a maximum of 1 week.

Environmental and Dietary Enrichments: The animals were given various cage-enrichment devices and dietary enrichment (that do not require analyses).

Randomization: The animals were arbitrarily selected based on pre-dose phase mean arterial pressure values.

The following table shows the group designation of the rats used in the study:

TABLE 3

| Group | Number of Male Rats | Day 1 | Day 8 | Day 15 | Day 22 |
|---|---|---|---|---|---|
| 1 | 1 | Combination 1 | Vehicle | Combination 3 | Combination 2 |
| 2 | 1 | Combination 2 | Combination 3 | Vehicle | Combination 1 |
| 3 | 1 | Combination 3 | Combination 1 | Combination 2 | Vehicle |
| 4 | 1 | Vehicle | Combination 2 | Combination 1 | Combination 3 |
| 5 | 1 | Vehicle | Combination 3 | Combination 2 | Combination 1 |
| 6 | 1 | Combination 3 | Combination 1 | Vehicle | Combination 2 |
| 7 | 1 | Combination 2 | Vehicle | Combination 1 | Combination 3 |
| 8 | 1 | Combination 1 | Combination 2 | Combination 3 | Vehicle |

The following table shows the dose levels administered in the study:

TABLE 4

| | Test Article | Dose Level (mg/kg/day) | Dose Concentration (mg/mL) | Dose Volume (mL/kg) |
|---|---|---|---|---|
| Combination 1 | Telmisartan | 0.17 | 0.017 | 10 |
| | Amlodipine Besylate | 0.22 | 0.022 | |
| | Indapamide | 0.08 | 0.008 | |
| Combination 2 | Telmisartan | 0.34 | 0.034 | 10 |
| | Amlodipine Besylate | 0.44 | 0.044 | |
| | Indapamide | 0.16 | 0.016 | |
| Combination 3 | Amlodipine Besylate | 0.44 | 0.044 | 10 |
| | Losartan Potassium | 0.31 | 0.031 | |
| | Hydrochlorothiazide | 1.74 | 0.174 | |
| Vehicle | 0.5% Methylcellulose (w/v), 0.25% polysorbate 80 (v/v), in phosphate buffer, pH 8 +/− 0.2 | 0 | 0 | 10 |

Dosing Procedures: For Combinations 1, 2 and 3, each test combination formulation was prepared fresh on each day of dosing. A portion of the vehicle (approximately 80%) was added to the test combination formulation and mixed until the preparations were homogenous. If a homogenous suspension or solution was not obtained, 1N NaOH and/or 1N HCl was added to adjust to pH 9+0.2. The remainder of the vehicle added and mixed with a stir bar. The test combination formulations were stirred continuously at room temperature and protected from light for approximately 30 minutes prior to and throughout dosing. The test combination formulations were stored protected from light, stirring in a refrigerator set to maintain 2 to 8° C.

Dosing Procedures: For pre-dose handling, the test combination formulations were allowed to equilibrate to approximately room temperature for at least 30 minutes prior to dosing. The animals were dosed at the volume of 10 mL/kg, and the actual dose volume was based on the most recent body weight. Oral gavage was used to administer the dose. The dose interval was once daily on Days 1, 8, 15, and 22. Following dose administration, the remaining test combination formulations were disposed of according to standard operating procedures.

Telemetry Collections: The animals were not disturbed or manipulated immediately prior to and during telemetry data collection without prior authorization. Such disturbances include but were not limited to cage changes, bedding changes, mopping, sanitation, or anything that would disturb the natural quiet environment that was important for collection of the cardiovascular telemetry data Animal Observation: Each rat was observed once daily in the morning. Any abnormal findings were recorded. The rats were observed for mortality, abnormalities, and signs of pain or distress. Any abnormal findings that were observed during the unscheduled observation periods were also noted.

Body Weight: The body weights were obtained at least once during the pre-dose phase and prior to each scheduled dose. Additional body weights were recorded to monitor animal health if appropriate. The animals were instrumented with a transmitter: a representative transmitter and leads were used to tare the balance prior to the collection of body weights for dose calculation purposes.

Telemetry Data Collection: The arterial pressure raw signals were digitized at a sampling rate of 500 Hz. Derived parameters in the pre-dose and dosing phases were the same. For pre-dose data collection, all implanted telemetry devices were checked for consistency of signal and to verify the telemetry signal was acceptable for analysis. The signal check consisted of at least one telemetry recording taken from each rat considered for the study. Telemetry data was recorded continuously for approximately 24 hours. The telemetry data was reviewed to determine if the rat was qualified for the study. The data was maintained in the study records and was used to calculate the nominal 24-hour mean arterial pressure average to support the randomization animal selection. For dosing phase data collection, continuous telemetry data was collected during the dosing phase starting at least 90 minutes prior to dosing through approximately 48 hours post-dose.

Nominal Dosing Time: The telemetry collection time points were based on a single nominal dosing time for all animals. The nominal dosing time for each day of the dosing phase were the end of dosing for the first half of animals dosed on that day recorded on each computer for all animals on that compute.

Telemetry Data Evaluation: Telemetry parameters, including heart rate (beats/minute), systolic pressure (mmHg), diastolic pressure (mmHg), mean arterial pressure (mmHg), and arterial pulse pressure (mmHg), were analyzed and reported. Telemetry data generated by Ponemah during the dosing phases were analyzed in 1-minute samples. Data was processed in 15-minute averages and were provided for data review. The 15-minute mean data was further averaged by binning into the following Analysis Periods:

Period 1: 0.5 to 2 hours post-dose;
Period 2: 2 to 4 hours post-dose;
Period 3: 4-8 hours post-dose;
Period 4: 8-12 hours post-dose;
Period 5: 12-20 hours post-dose;
Period 6: 20-32 hours post-dose (second light cycle); and
Period 7: 32 to 44 hours post-dose (second dark cycle).

Analysis

Blood pressure was measured over a 44-hour period using an implanted telemetry device. The primary outcome was systolic blood pressure.

Statistical analyses were conducted using all available data points, with weighting to reflect the non-uniform timing of measurements. Estimates of treatment effects were calculated using estimated differences between treatments using a mixed model (SAS 9.4, SAS Institute, Cary, NC) with a direct product autoregressive correlation structure to account for repeated measurements within individuals over time.

Results

Eight animals began the study; however, the telemetry transmitter failed in one animal. As a result, complete data was available from seven animals.

The following table shows the differences in systolic BP (mmHg) between treatments:

TABLE 5

| Comparison Overall difference between treatments | Level | Estimate (95% CI) | P-value 0.0004 |
|---|---|---|---|
| Systolic BP (95% CI) | Control | 177.4 (174.4-180.3) | — |
| | Combination 1 | 172.1 (169.3-174.9) | — |
| | Combination 2 | 169.0 (166.1-171.9) | — |
| | Combination 3 | 175.4 (172.5-178.3) | — |
| Treatment comparisons | Control vs Combination 1 | −5.3 (−8.7-1.8) | 0.0048 |
| | Control vs Combination 2 | −8.4 (−11.5-5.2) | <.0001 |
| | Control vs Combination 3 | −2.0 (−5.6-1.7) | 0.2663 |
| | Combination 1 vs Combination 2 | −3.1 (−6.5-0.3) | 0.0720 |
| | Combination 1 vs Combination 3 | 3.3 (0.3-6.3) | 0.0342 |
| | Combination 2 vs Combination 3 | 6.4 (3.0-9.8) | 0.0009 |

Figure 2:
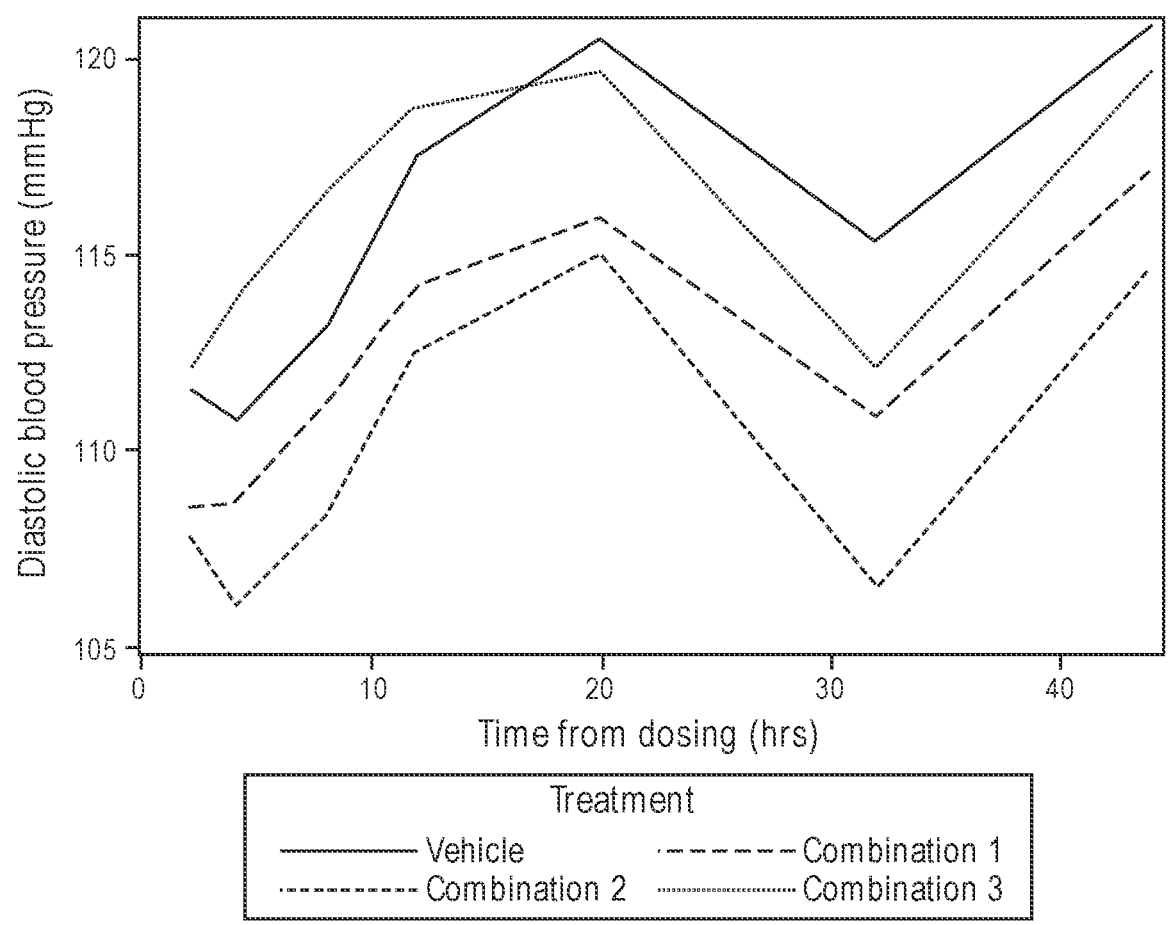
FIG. 2 shows the mean diastolic blood pressure (mmHg) across time periods by treatment.
Figure 3:
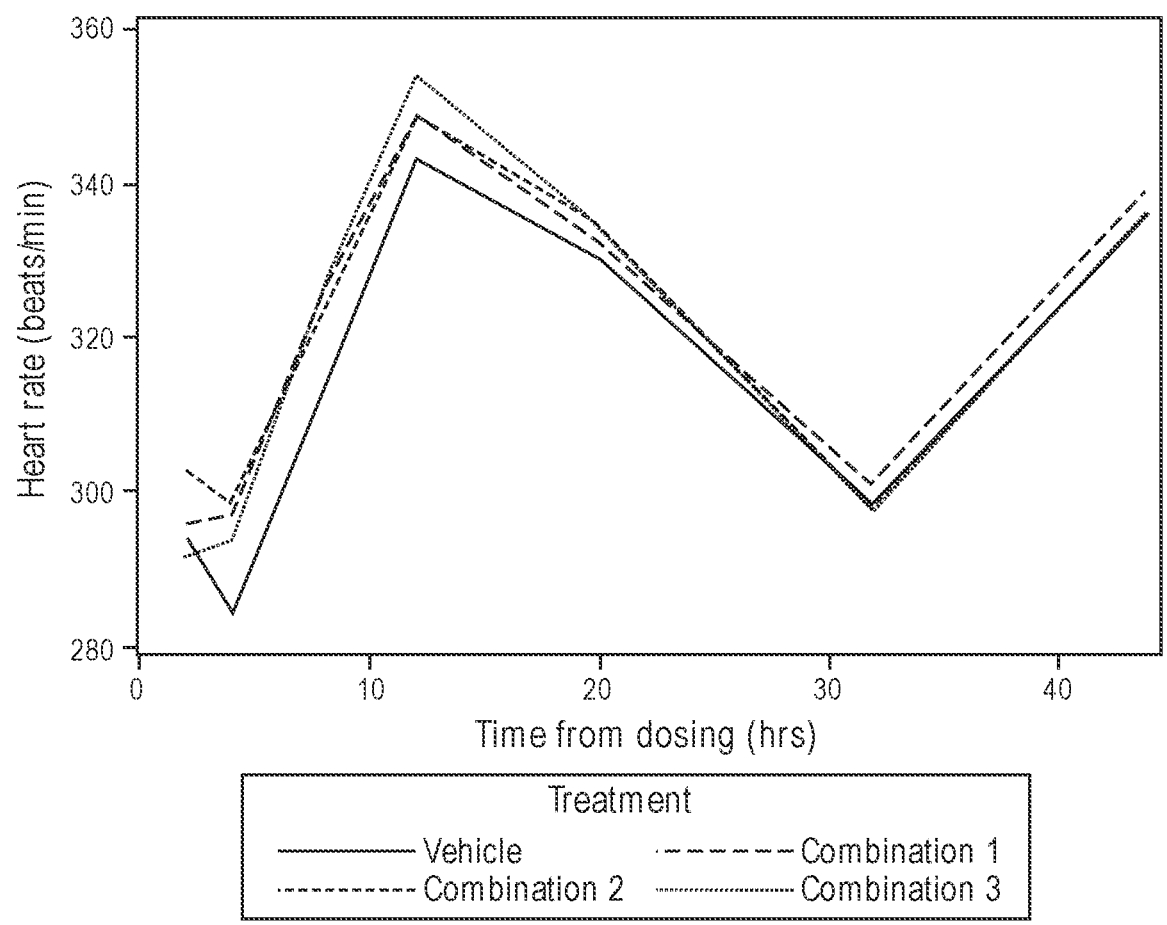
FIG. 3 shows the mean heart rate across time periods by treatment.

FIG. 1 shows the mean systolic blood pressure (mmHg) across time periods by treatment. FIG. 2 shows the mean diastolic blood pressure (mmHg) across time periods by treatment. FIG. 3 shows the mean heart rate across time periods by treatment.

In this non-limiting example, the results demonstrated that Combination 1 produced significantly larger reductions in systolic blood pressure than Combination 3, and Combination 2 produced significantly larger reductions in systolic blood pressure than either Combination 3 or 1. These differences persisted over the full 44-hour period of observation. The results demonstrated that both Combination 1 and Combination 2 produced significantly larger reductions in systolic blood pressure than Combination 3. These differences persisted over the full 44-hour period of observation. There were similar differences between the three combinations in the reduction in DPB, and no differences between the combinations in heart rate.

In this non-limiting example, these results demonstrate unexpected differences between the telmisartan, amlodipine besylate, indapamide combinations and the losartan, amlodipine besylate, hydrochlorothiazide combination. Specifically, at equivalent or lower doses, the telmisartan, amlodipine besylate, and indapamide combination produced significantly larger reductions in blood pressure than the combination of losartan, amlodipine besylate, and hydrochlorothiazide. As the amlodipine besylate dose was the same in Combination 2 and 3, the results demonstrate previously unknown differences in the effectiveness of specific angiotensin II receptor blockers and specific diuretics (such as a thiazide diuretic versus a thiazide-like diuretic) when provided in parallel with amlodipine besylate.

Example 2: Triple Combination Composition Therapy for the Treatment of Hypertension Methods This study is a randomized, placebo-controlled, double-blind cross-over trial. The study is divided into three phases. During the first phase (4 weeks) participants are randomized (1:1) to either receive the triple combination composition therapy or Placebo. This is followed by a two week washout (placebo) and subsequently participants are crossed over to the opposite arm to receive the other treatment for four weeks. Participants are recruited from the community, predominantly through community general practices in western Sydney, Australia.

Participants

Participants are eligible if they met the following inclusion criteria: 1) adults aged 18 years and over, 2) office SBP>140 mmHg and/or DBP>90 mmHg on 2 readings on separate days; plus baseline ambulatory SBP>135 and/or DBP>85; 3) Not on medical treatment for hypertension. Exclusion criteria included: No definite contraindication to one or more component medications in the triple combination composition; the responsible clinician felt a change in current therapy would place the patient at risk; severe or accelerated hypertension; pregnancy; inability to provide informed consent; and medical illness with anticipated life expectancy less than 3 months.

Intervention

For these studies, either the triple combination with each component at 50% of the lowest hypertension therapeutic dose (LHTD) or the triple combination with each component at 100% of the lowest hypertension therapeutic dose (LHTD) will be tested.

If the study is testing the triple combination with each component at 50% of the lowest hypertension therapeutic dose (LHTD), then the test composition is as follows. The triple combination composition is a single encapsulated pill containing the three following components in the specified amounts: telmisartan 10 mg, amlodipine besylate 1.25 mg, and indapamide 0.625 mg. The placebo capsule appears identical and contains placebo tablets of similar weight to those in the triple combination composition.

If the study is testing the triple combination with each component at 100% of the lowest hypertension therapeutic dose (LHTD), then the test compositions is as follow. The triple combination composition is a single encapsulated pill containing the three following components in the specified amounts: telmisartan 20 mg, amlodipine besylate 2.5 mg, and indapamide 1.25 mg. The placebo capsule appears identical and contains placebo tablets of similar weight to those in the triple combination composition.

Participants are administered a single pill, triple combination composition or placebo, throughout the trial. Patients are instructed to take the tablets at the same time each day and are encouraged to take this in the morning, but the time of the day (morning or evening) is at the patient's preference.

All trial medicines are prepared by a TGA-cGMP (Therapeutic Goods Australia—certificate of Good Manufacturing Practice) licensed manufacturing facility. If appropriate, low strength doses are obtained by halving half-strength doses using a pill splitting device, without crushing, and are weighed to ensure accuracy of halving doses. The low strength doses are than encapsulated using gelatin capsules (DBCaps-Capsugel). The capsules are stored in a cool dry place and monitored using temperature loggers, until they are dispensed.

Treatment allocations are blinded to both study staff and participants. In addition to the study drugs, all participants are offered education on healthier lifestyle options as recommended by guidelines for hypertension management.

Randomization

A computer assisted randomization sequence is generated by a statistician and supplied to the pharmaceutical packaging company. The research assistant, recruitment team, investigators are blinded to this sequence. For each patient i.e. allocated randomization number, the pills are packaged into three child-resistant packs corresponding to three phases of the study. All packs have identical appearance ensuring blinding of patient and research staff. Subsequently the medication packs are prescribed in an organized sequence.

Outcomes and Data Collection

The primary outcome is reduction in mean 24 hour systolic blood pressure at 4 weeks using ambulatory blood pressure monitoring (ABP). The secondary outcomes include:
 a. Reduction in mean 24 hour diastolic blood pressure, and in daytime and nighttime SBP and DBP at 4 weeks
 b. Reduction in office SBP and DBP as measured by a standardized automated blood pressure cuff
 c. Proportion with controlled blood pressure at 4 weeks, defined as <135/85 mmHg 24 hour BP and <140/90 mmHg office BP
 d. Adverse events and pre-specified adverse events by laboratory parameters: Rise in transaminases (ALT/AST) more than 3× upper limit of normal or doubling if baseline levels known to be elevated; drop in estimated glomerular filtration rate by >20% as estimated from serum creatinine; sodium, potassium and uric acid levels
 e. Assessment of acceptability and tolerability Patients will undergo 24 hour ABP monitoring 4 times—baseline (off study drug), 4 weeks (on phase 1 drug), 6 weeks (on placebo), and 10 weeks (on phase 3 drug). In order to minimize inconvenience, patients are referred for ABP to a lab. The ABP units are calibrated at regular intervals by the lab according to the manufacturer's specification. To minimize variability, the follow up readings are repeated from the same collection center using the same brand device. Participants are reimbursed nominal amounts to cover travel and parking costs. Study medications and investigations are provided at no cost to participants. Office BP is recorded three times at each visit using an OMRON T9P (HEM-759-C1). The second and the third readings are averaged for study analysis. In addition at week 4 and 10 patients will undergo blood tests to assess for biochemical side effects, are administered a questionnaire for clinical side effects, and compliance is assessed by self-report and pill count. Patients will remain blinded to their treatment allocation when completing this questionnaire.

Drug acceptability and tolerability are also assessed at the end of the study. All adverse events are recorded. In addition, clinical adverse events possibly associated with blood pressure lowering medications: dizziness, blurred vision, syncope/collapse, chest pain/angina, shortness of breath, cough, wheeze, pedal oedema, skin rash, itching are specifically asked about.

The trial has a simplified data safety and management committee of two core members with expertise in clinical medicine, trials and statistics. A single meeting convenes when 10 patients are randomized to the trial to review safety, and the study is advised to continue.

Statistical Considerations

A sample size of 50 patients is planned to provide 90% power at $p=0.05$ to detect a SBP difference of 12 mmHg between the intervention and control assuming a SD of the within patient difference of 12 mmHg, taking into account the possibility of a 10% loss to follow-up.

Statistical Approach

Analyses are conducted on an intention to treat basis. All tests are two-sided and the nominal level of a is 5%. All statistical analyses are unadjusted for prognostic covariates. We will report compliance to the study drug using data on pills (doses) taken and missed doses over the time period.

A linear mixed model is used to estimate the effect of the treatment on change in blood pressure from baseline for each treatment period, according to the Kenward and Roger approach (Kenward M G, Roger J H. The use of baseline covariates in crossover studies. *Biostatistics* 2010; 11(1): 1-17.) In order to appropriately adjust for baseline levels, collected at the beginning of each treatment period (week 0, week 6), this method uses all measurements (baseline and follow-up, in both period) as outcomes, but accounts for covariance between measurements within individuals (Liu G F, Lu K, Mogg R, Mallick M, Mehrotra D V. Should baseline be a covariate or dependent variable in analyses of change from baseline in clinical trials? Stat Med 2009; 28(20): 2509-30). A linear contrast between the variables denoting period (first/second), type of measurement (baseline/final), and treatment received (placebo/triple combination composition) produces an unbiased estimate of effect of the triple combination composition on change in blood pressure compared to the placebo. All available data are included in the model, no missing data is imputed. If a patient is missing data for one period, data from the available period are used. A sensitivity analysis is carried including only patients with data available from both periods to see if the effect of treatment is modified. There is also adjustment of the denominator degrees of freedom of Kenward and Roger (2009) that is optimal for smaller sample sizes (Kenward M G, Roger J H. An improved approximation to the precision of fixed effects from restricted maximum likelihood. Computational Statistics & Data Analysis 2009; 53(7): 2583-95).

Testing for carry over will use an unpaired t-test of the main outcome with order as an effect. Period effect is tested by using a paired t-test comparing the main outcome in period 1 with main outcome in period 2 from the same patient. A sensitivity analysis is also performed using normal paired t-test to compare primary outcome between different period (different treatment) from the same patient, ignoring the baseline level of each period.

Continuous secondary endpoints with baseline values (e.g., daytime/night-time ambulatory SBP/DBP) are analyzed similarly to the primary endpoint. Other continuous variables without a baseline value in each period are analyzed with a paired t-test. Counts and percentages of all adverse events are reported. As a sensitivity analysis, the analyses are repeated on the complete cases (i.e. full data for each measurement period).

Tests for interaction of treatment effect with age (<=60 vs. >60 years), gender, and BMI (<=30 vs. <30 kg/m$^2$). Subgroup analyses for each variable are also conducted. All analyses are conducted using SAS 9.4 (Cary, NC, USA) on software.

Example 3: Comparative Study of Triple Combination Versus Standard Dose Monotherapy for the Treatment of Hypertension Objectives The primary objective of this study is to investigate in a double blind randomized controlled trial whether initiating treatment with a triple combination therapy will lower blood pressure more effectively, and with fewer side effects, compared to initiating standard dose monotherapy as per current guidelines in patients with hypertension. The secondary objective is to assess if this approach is safe and has fewer side effects compared to standard care.

Study Design

This will be a 12-week double blind randomized controlled trial (1:1) of 650 patients with grade 1 and 2 essential hypertension. Subjects will be randomized through a central computer-based randomization service, to initial therapy with the triple combination composition or to an angiotensin receptor blocker (ARB), with option to add a calcium channel blocker (CCB) as required, as per current Australian Hypertension guidelines. The primary outcome will be reduction in mean systolic blood pressure using standardized automated BP cuff at 12 weeks. Secondary outcomes will include: proportion with controlled blood pressure at 6 weeks, 12 weeks, ambulatory blood pressure (ABP) measures and tolerability/occurrence of adverse events.

Eligibility Criteria

The inclusion criteria are as follows:
  Adults (≥18 years)
  Treatment naïve, or currently not on treatment (not taken in last 4 weeks), or taking one BP lowering drug (angiotensin converting enzyme inhibitor, angiotensin receptor blocker, calcium channel blocker, beta-blocker, aldosterone antagonist, alpha-blocker)
  SBP 140-179 mmHg and/or DBP 90-109 mmHg documented on two occasions more than a week apart
  At least one of the measures should be documented by study staff with study automatic BP device OR recorded as daytime average SBP≥135 mmHg and/or DBP≥85 mmHg on 24 hour ambulatory BP monitoring
  At least one of these measures should be recent (in last 12 weeks)
  24 hour Ambulatory BP monitoring daytime average SBP≥135 mmHg and/or DBP≥85 mmHg—documented within 12 weeks of randomization The exclusion criteria are as follows:
  Contraindication to telmisartan, amlodipine, or indapamide
  Evidence of secondary cause of hypertension e.g. renal artery stenosis; Significant renal impairment (eGRF<50), raised serum potassium (above lab normal limit)
  Women who are pregnant, breast feeding and/or of childbearing potential and not using medically acceptable form of contraception throughout the study (pharmacological or barrier methods)
  Concomitant illness, physical impairment or mental condition which in the opinion of the study team/primary care physician could interfere with the conduct of the study including outcome assessments
  Participation in a concurrent interventional medical investigation or clinical trial. Patients in observational, natural history and/or epidemiological studies not involving an intervention are eligible.
  Participant's responsible primary care or other responsible physician believes it is not appropriate for participant to switch current monotherapy
  Inability or unwillingness to provide written informed consent
  Unable to complete study procedures including 24 hour Ambulatory BP
  Definite indication for combination therapy Study Treatment For these studies, either the triple combination with each component at 50% of the lowest hypertension therapeutic dose (LHTD) or the triple combination with each component at 100% of the lowest hypertension therapeutic dose (LHTD) will be tested.

If the study is testing the triple combination with each component at 50% of the lowest hypertension therapeutic dose (LHTD), then the test composition is as follows. Patients who meet criteria for inclusion will be randomized to: 1) A combination pill comprising the following three components—telmisartan 10 mg, amlodipine besylate 1.25 mg, and indapamide 0.625 mg; or 2) telmisartan 40 mg.

If the study is testing the triple combination with each component at 100% of the lowest hypertension therapeutic dose (LHTD), then the test composition is as follows. Patients who meet criteria for inclusion will be randomized to: 1) A combination pill comprising the following three components—telmisartan 20 mg, amlodipine besylate 2.5 mg, and indapamide 1.25 mg; or 2) telmisartan 40 mg.

Patients who are currently on monotherapy will be asked to stop their treatment while they are taking the study treatment. At 6 weeks if the BP is greater than 140/90 mmHg in either arm amlodipine besylate (5 mg) will be added by study staff.

Outcomes

The primary outcome will be the difference between groups in mean automated office systolic blood pressure at 12 weeks adjusted for baseline values.

The secondary outcomes include the following:
The 24-hour ambulatory blood pressure measures
  a. Difference between groups in mean 24-hour SBP and DBP at 12 weeks
  b. Difference between groups in mean change in 24-hour SBP and DBP from 0 to 12 weeks
  c. Difference between groups in mean daytime SBP and DBP at 12 weeks Difference between groups in mean night-time SBP and DBP at 12 weeks
  d. Difference between groups in daytime, night-time, and 24 hour BP load (percentage area under the blood pressure curve above normal day, night, and 24 hour values as per NHFA Guide to management of hypertension 2008)
  e. Difference between groups in the proportion of non-dippers (night-time BP is not more than 10% lower than average daytime BP as per NHFA Guide to management of hypertension 2008) and coefficient of variability of BP (O'Brien, E., G. Parati, and G. Stergiou, Hypertension, 2013. 62(6): p. 988-94).

Other blood pressure measures in the triple group vs control groups:
  a. Change in mean diastolic blood pressure from baseline to 12 weeks,
  b. Hypertension control (% with SBP<140 mmHg and DBP<90 mmHg) at 6 and 12 weeks, c. Percentage requiring step-up treatment at 6 weeks
d. Percentage with both BP control (as defined above) and no adverse events.
e. Difference between groups in SBP and DBP variability Tolerability
   a. Difference between groups in potentially related side-effects (dizziness, blurred vision, syncope/collapse/fall, chest pain/angina, shortness of breath, cough, wheeze, ankle oedema, skin rash, itching, gout, hyperkalaemia, hypokalaemia, hyponatraemia, other)
   b. Difference between groups in mean potassium, uric acid, blood glucose, cholesterol and fractions, ALT, AST, UACR (Urine albumin-to-creatinine ratio) and creatinine levels.
   c. Difference between groups in participant withdrawals from treatment Statistical Methods All analyses of study outcomes will be conducted according to the principle of intention-to-treat. The primary analysis of change in systolic blood pressure (SBP) at 12 weeks will be performed using an analysis of covariance (ANCOVA) including the treatment arm and baseline SBP as a covariate. Continuous secondary outcomes will be analyzed similarly. Additional analyses will include both 6-week and 12-week measurements in a longitudinal model including treatment arm, visit, and treatment by visit interaction as well as the baseline measurement. Within-patient correlations will be modelled using generalized estimating equations. A similar approach will be applied to binary endpoints (e.g. hypertension control) with log-binomial regression used in place of linear regression. There will also be pre-defined subgroup analyses, including by baseline blood pressure, gender, age, and hypertension treatment history. A detailed analysis plan will be developed prior to unblinding.

Example 4: Pharmaceutical Compositions 1

The following pharmaceutical compositions are prepared with the specified components and doses as shown in the following table.

TABLE 6

| Agent | Proposed Dose (mg) | Proposed Dose Range (mg) |
|---|---|---|
| Composition A | | |
| Amlodipine besylate | 1.25 | 1-1.5 |
| Hydrochlorothiazide | 6.25 | 5-7.5 |
| Telmisartan | 10 | 8-12 |
| Composition B | | |
| Amlodipine besylate | 1.25 | 1-1.5 |
| Indapamide | 0.625 | 0.5-0.75 |
| Telmisartan | 10 | 8-12 |
| Composition C | | |
| Amlodipine besylate | 1.25 | 1-1.5 |
| Chlorthalidone | 12.5 | 10-15 |
| Telmisartan | 10 | 8-12 |
| Composition D | | |
| Amlodipine besylate | 1.25 | 1-1.5 |
| Chlorthalidone | 12.5 | 10-15 |
| Irbesartan | 37.5 | 30-45 |

Example 5: Pharmaceutical Compositions 2

The following pharmaceutical compositions are prepared with the specified components and doses as shown in the following table.

TABLE 7

| Agent | Proposed Dose (mg) | Proposed Dose Range (mg) |
|---|---|---|
| Composition E | | |
| Amlodipine besylate | 1.65 | 1.5-2 |
| Hydrochlorothiazide | 8.25 | 7.5-10 |
| Irbesartan | 49.5 | 45-60 |
| Composition F | | |
| Amlodipine besylate | 1.65 | 1.5-2 |
| Indapamide | 0.825 | 0.75-1.0 |
| Irbesartan | 49.5 | 45-60 |
| Composition G | | |
| Amlodipine besylate | 1.65 | 1.5-2 |
| Hydrochlorothiazide | 8.25 | 7.5-10 |
| Telmisartan | 13.2 | 12-16 |
| Composition H | | |
| Amlodipine besylate | 1.65 | 1.5-2 |
| Indapamide | 0.825 | 0.75-1.0 |
| Telmisartan | 13.2 | 12-16 |
| Composition I | | |
| Amlodipine besylate | 1.65 | 1.5-2 |
| Chlorthalidone | 16.5 | 15-20 |
| Telmisartan | 13.2 | 12-16 |
| Composition J | | |
| Amlodipine besylate | 1.65 | 1.5-2 |
| Chlorthalidone | 16.5 | 15-20 |
| Irbesartan | 49.5 | 45-60 |

Example 6: Pharmaceutical Compositions 3

The following pharmaceutical compositions are prepared with the specified components and doses as shown in the following table.

TABLE 8

| Agent | Proposed Dose (mg) | Proposed Dose Range (mg) |
|---|---|---|
| Composition K | | |
| Amlodipine besylate | 2.5 | 2-3.75 |
| Hydrochlorothiazide | 12.5 | 10-18.75 |
| Irbesartan | 75 | 60-112.5 |
| Composition L | | |
| Amlodipine besylate | 2.5 | 2-3.75 |
| Indapamide | 1.25 | 1-1.875 |
| Irbesartan | 75 | 60-112.5 |
| Composition M | | |
| Amlodipine besylate | 2.5 | 2-3.75 |
| Hydrochlorothiazide | 12.5 | 10-18.75 |
| Telmisartan | 20 | 16-30 |
| Composition N | | |
| Amlodipine besylate | 2.5 | 2-3.75 |
| Indapamide | 1.25 | 1-1.875 |
| Telmisartan | 20 | 16-30 |

TABLE 8-continued

| Agent | Proposed Dose (mg) | Proposed Dose Range (mg) |
|---|---|---|
| Composition O | | |
| Amlodipine besylate | 2.5 | 2-3.75 |
| Chlorthalidone | 25 | 20-37.5 |
| Telmisartan | 20 | 16-30 |
| Composition P | | |
| Amlodipine besylate | 2.5 | 2-3.75 |
| Chlorthalidone | 25 | 20-37.5 |
| Irbesartan | 75 | 60-112.5 |

Embodiments

Embodiment 1. A pharmaceutical composition comprising
(a) an angiotensin II receptor blocker;
(b) a diuretic; and
(c) a calcium channel blocker
wherein the dose of each (a), (b), and (c) is from about 40% to about 80% of the lowest hypertension therapeutic dose (LHTD) for each of the (a), (b), and (c).

Embodiment 2. The pharmaceutical composition of embodiment 1, wherein the pharmaceutical composition comprises a blood pressure lowering combination of blood pressure lowering active agents, wherein the blood pressure lowering active agents consists of an angiotensin II receptor blocker, a diuretic, and a calcium channel blocker.

Embodiment 3. The pharmaceutical composition of embodiments 1 or 2, wherein the pharmaceutical composition is essentially free of an angiotensin-converting enzyme inhibitor or a pharmaceutically acceptable salt thereof.

Embodiment 4. The pharmaceutical composition of any one of embodiments 1-3, wherein the pharmaceutical composition is essentially free of a beta-blocker or a pharmaceutically acceptable salt thereof.

Embodiment 5. The pharmaceutical composition of any one of embodiments 1-4, wherein the pharmaceutical composition is essentially free of a lipid-regulating agent, platelet function-altering agent, a serum homocysteine-lowering agent, or a combination thereof.

Embodiment 6. The pharmaceutical composition of embodiment 5, wherein the pharmaceutical composition is essentially free of a lipid-regulating agent.

Embodiment 7. The pharmaceutical composition of embodiment 6, wherein the lipid-regulating agent is atorvastatin, simvastatin, cerivastatin, fluvastatin, or pravastatin.

Embodiment 8. The pharmaceutical composition of embodiments 6 or 7, wherein the lipid-regulating agent is atorvastatin or simvastatin.

Embodiment 9. The pharmaceutical composition of embodiment 5, wherein the pharmaceutical composition is essentially free of a platelet function-altering agent.

Embodiment 10. The pharmaceutical composition of embodiment 9, wherein the platelet function-altering agent is aspirin, ticlopidine, dipyridamole, clopidogrel, abciximab, or ibuprofen.

Embodiment 11. The pharmaceutical composition of embodiments 9 or 10, wherein the platelet function-altering agent is aspirin.

Embodiment 12. The pharmaceutical composition of embodiment 5, wherein the pharmaceutical composition is essentially free of a serum homocysteine-lowering agent.

Embodiment 13. The pharmaceutical composition of embodiment 12, wherein the serum homocysteine-lowering agent is folic acid, vitamin B6, vitamin B12, or a combination thereof.

Embodiment 14. The pharmaceutical composition of embodiments 12 or 13, wherein the serum homocysteine-lowering agent is folic acid.

Embodiment 15. The pharmaceutical composition of any one of embodiments 1-14, wherein the diuretic is a thiazide diuretic.

Embodiment 16. The pharmaceutical composition of embodiment 15, wherein the thiazide diuretic is altizide, bendroflumethiazide, chlorothiazide, cyclopenthiazide, cyclothiazide, epitizide, hydrochlorothiazide, hydroflumethiazide, mebutizide, methyclothiazide, polythiazide, trichlormethiazide, or the pharmaceutically acceptable salt or hydrate thereof.

Embodiment 17. The pharmaceutical composition of embodiment 16, wherein the thiazide diuretic is hydrochlorothiazide.

Embodiment 18. The pharmaceutical composition of any one of embodiments 1-14, wherein the diuretic is a thiazide-like diuretic.

Embodiment 19. The pharmaceutical composition of embodiment 18, wherein the thiazide-like diuretic is quinethazone, clopamide, chlorthalidone, mefruside, clofenamide, metolazone, meticrane, xipamide, indapamide, clorexolone, fenquizone, or the pharmaceutically acceptable salt or hydrate thereof.

Embodiment 20. The pharmaceutical composition of embodiment 19, wherein the thiazide-like diuretic is indapamide or the hydrate thereof.

Embodiment 21. The pharmaceutical composition of embodiment 20, wherein the thiazide-like diuretic is indapamide.

Embodiment 22. The pharmaceutical composition of embodiment 19, wherein the thiazide-like diuretic is chlorthalidone.

Embodiment 23. The pharmaceutical composition of any one of embodiments 1-14, wherein the diuretic is a loop diuretic.

Embodiment 24. The pharmaceutical composition of embodiment 23, wherein the loop diuretic is furosemide, bumetanide, etacrynic acid, etozolin, muzolimine, ozolinone, piretanide, tienilic acid, torasemide, or the pharmaceutically acceptable salt or hydrate thereof.

Embodiment 25. The pharmaceutical composition of any one of embodiments 1-14, wherein the diuretic is dichlorphenamide, amiloride, pamabrom, mannitol, acetazolamide, methazolamide, spironolactone, triamterene, or the pharmaceutically acceptable salt or hydrate thereof.

Embodiment 26. The pharmaceutical composition of any one of embodiments 1-25, wherein the calcium channel blocker is amlodipine, nifedipine, diltiazem, nimodipine, verapamil, isradipine, felodipine, nicardipine, nisoldipine, clevidipine, dihydropyridine, lercanidipine, nitrendipine, cilnidipine, manidipine, mibefradil, bepridil, barnidipine, nilvadipine, gallopamil, lidoflazine, aranidipine, dotarizine, diproteverine, or the pharmaceutically acceptable salt or hydrate thereof.

Embodiment 27. The pharmaceutical composition of embodiment 26, wherein the calcium channel blocker is amlodipine or the pharmaceutically acceptable salt thereof.

Embodiment 28. The pharmaceutical composition of embodiment 27, wherein the calcium channel blocker is amlodipine besylate.

Embodiment 29. The pharmaceutical composition of any one of embodiments 1-28, wherein the angiotensin II receptor blocker is irbesartan, telmisartan, valsartan, candesartan, eprosartan, olmesartan, azilsartan, losartan, or the pharmaceutically acceptable salt or hydrate thereof.

Embodiment 30. The pharmaceutical composition of embodiment 29, wherein the angiotensin II receptor blocker is irbesartan.

Embodiment 31. The pharmaceutical composition of embodiment 29, wherein the angiotensin II receptor blocker is telmisartan.

Embodiment 32. The pharmaceutical composition of any one of embodiments 1-31, wherein the dose of each (a), (b), and (c) is from about 40% to about 60% of the lowest hypertension therapeutic dose (LHTD) for each of the (a), (b), and (c).

Embodiment 33. The pharmaceutical composition of embodiment 32, wherein the diuretic is a thiazide diuretic, and the dose of the thiazide diuretic is about 50% of the lowest hypertension therapeutic dose (LHTD) for the thiazide diuretic.

Embodiment 34. The pharmaceutical composition of embodiment 33, wherein the thiazide diuretic is hydrochlorothiazide, and the dose of the hydrochlorothiazide is about 6.25 mg.

Embodiment 35. The pharmaceutical composition of embodiment 32, wherein the diuretic is a thiazide-like, and the dose of the thiazide-like diuretic is about 50% of the lowest hypertension therapeutic dose (LHTD) for the thiazide-like diuretic.

Embodiment 36. The pharmaceutical composition of embodiment 35, wherein the thiazide-like diuretic is indapamide, and the dose of the indapamide is about 0.625 mg.

Embodiment 37. The pharmaceutical composition of embodiment 35, wherein the thiazide-like diuretic is chlorthalidone, and the dose of the chlorthalidone is about 12.5 mg.

Embodiment 38. The pharmaceutical composition of embodiment 32, wherein the diuretic is a loop diuretic, and the dose of the loop diuretic is about 50% of the lowest hypertension therapeutic dose (LHTD) for the loop-diuretic.

Embodiment 39. The pharmaceutical composition of any one of embodiments 32-38, wherein the dose of the calcium channel blocker is about 50% of the lowest hypertension therapeutic dose (LHTD) for the calcium channel blocker.

Embodiment 40. The pharmaceutical composition of embodiment 39, wherein the calcium channel blocker is amlodipine besylate, and the dose of amlodipine besylate is about 1.25 mg.

Embodiment 41. The pharmaceutical composition of any one of embodiments 32-40, wherein the dose of the angiotensin II receptor blocker is about 50% of the lowest hypertension therapeutic dose (LHTD) for the angiotensin II receptor blocker.

Embodiment 42. The pharmaceutical composition of embodiment 41, wherein the angiotensin II receptor blocker is irbesartan, and dose of the irbesartan is about 37.5 mg.

Embodiment 43. The pharmaceutical composition of embodiment 41, wherein the angiotensin II receptor blocker is telmisartan, and the dose of the telmisartan is about 10 mg.

Embodiment 44. The pharmaceutical composition of embodiment 32, wherein the angiotensin II receptor blocker is irbesartan, the diuretic is hydrochlorothiazide, and the calcium channel blocker is amlodipine besylate.

Embodiment 45. The pharmaceutical composition of embodiment 44, wherein the dose of irbesartan is from about 30 mg to about 45 mg, the dose of hydrochlorothiazide is from about 5 mg to about 7.5 mg, and the dose of amlodipine besylate is from about 1 mg to about 1.5 mg.

Embodiment 46. The pharmaceutical composition of embodiment 45, wherein the dose of irbesartan is about 37.5 mg, the dose of hydrochlorothiazide is about 6.25 mg, and the dose of amlodipine besylate is about 1.25 mg.

Embodiment 47. The pharmaceutical composition of embodiment 32, wherein the angiotensin II receptor blocker is telmisartan, the diuretic is hydrochlorothiazide, and the calcium channel blocker is amlodipine besylate.

Embodiment 48. The pharmaceutical composition of embodiment 47, wherein the dose of telmisartan is from about 8 mg to about 12 mg, the dose of hydrochlorothiazide is from about 5 mg to about 7.5 mg, and the dose of amlodipine besylate is from about 1 mg to about 1.5 mg.

Embodiment 49. The pharmaceutical composition of embodiment 48, wherein the dose of telmisartan is about 10 mg, the dose of hydrochlorothiazide is about 6.25 mg, and the dose of amlodipine besylate is about 1.25 mg.

Embodiment 50. The pharmaceutical composition of embodiment 32, wherein the angiotensin II receptor blocker is irbesartan, the diuretic is indapamide, and the calcium channel blocker is amlodipine besylate.

Embodiment 51. The pharmaceutical composition of embodiment 50, wherein the dose of irbesartan is from about 30 mg to about 45 mg, the dose of indapamide is from about 0.5 mg to about 0.75 mg, and the dose of amlodipine besylate is from about 1 mg to about 1.5 mg.

Embodiment 52. The pharmaceutical composition of embodiment 51, wherein the dose of irbesartan is about 37.5 mg, the dose of indapamide is about 0.625 mg, and the dose of amlodipine is about 1.25 mg.

Embodiment 53. The pharmaceutical composition of embodiment 32, wherein the angiotensin II receptor blocker is telmisartan, the diuretic is indapamide, and the calcium channel blocker is amlodipine besylate.

Embodiment 54. The pharmaceutical composition of embodiment 53, wherein the dose of telmisartan is from about 8 mg to about 12 mg, the dose of indapamide is from about 0.5 mg to about 0.75 mg, and the dose of amlodipine besylate is from about 1 mg to about 1.5 mg.

Embodiment 55. The pharmaceutical composition of embodiment 54, wherein the dose of telmisartan is about 10 mg, the dose of indapamide is about 0.625 mg, and the dose of amlodipine besylate is about 1.25 mg.

Embodiment 56. The pharmaceutical composition of embodiment 32, wherein the angiotensin II receptor blocker is telmisartan, the diuretic is chlorthalidone, and the calcium channel blocker is amlodipine besylate.

Embodiment 57. The pharmaceutical composition of embodiment 56, wherein the dose of telmisartan is from about 8 mg to about 12 mg, the dose of chlorthalidone is from about 10 mg to about 15 mg, and the dose of amlodipine besylate is from about 1 mg to about 1.5 mg.

Embodiment 58. The pharmaceutical composition of embodiment 57, wherein the dose of telmisartan is about 10 mg, the dose of chlorthalidone is about 12.5 mg, and the dose of amlodipine besylate is about 1.25 mg.

Embodiment 59. The pharmaceutical composition of embodiment 32, wherein the angiotensin II receptor blocker is irbesartan, the diuretic is chlorthalidone, and the calcium channel blocker is amlodipine besylate.

Embodiment 60. The pharmaceutical composition of embodiment 59, wherein the dose of irbesartan is from about 30 mg to about 45 mg, the dose of chlorthalidone is from about 10 mg to about 15 mg, and the dose of amlodipine besylate is from about 1 mg to about 1.5 mg.

Embodiment 61. The pharmaceutical composition of embodiment 60, wherein the dose of irbesartan is about 37.5 mg, the dose of chlorthalidone is about 12.5 mg, and the dose of amlodipine besylate is about 1.25 mg.

Embodiment 62. The pharmaceutical composition of any one of embodiments 1-31, wherein the dose of each (a), (b), and (c) is from about 60% to about 80% of the lowest hypertension therapeutic dose (LHTD) for each of the (a), (b), and (c).

Embodiment 63. The pharmaceutical composition of embodiment 62, wherein the diuretic is thiazide diuretic, and dose of the thiazide diuretic is about 66% of the lowest hypertension therapeutic dose (LHTD) for the thiazide diuretic.

Embodiment 64. The pharmaceutical composition of embodiment 63, wherein the thiazide diuretic is hydrochlorothiazide, and the dose of the hydrochlorothiazide is about 8.25 mg.

Embodiment 65. The pharmaceutical composition of embodiment 62, wherein the diuretic is thiazide-like diuretic, and dose of the thiazide-like diuretic is about 66% of the lowest hypertension therapeutic dose (LHTD) for the thiazide-like diuretic.

Embodiment 66. The pharmaceutical composition of embodiment 65, wherein the thiazide-like diuretic is indapamide, and the dose of the indapamide is about 0.825 mg.

Embodiment 67. The pharmaceutical composition of embodiment 65, wherein the thiazide-like diuretic is chlorthalidone, and the dose of the chlorthalidone is about 16.5 mg.

Embodiment 68. The pharmaceutical composition of embodiment 62, wherein the diuretic is loop diuretic, and the dose of the loop diuretic is about 66% of the lowest hypertension therapeutic dose (LHTD) for the loop-diuretic.

Embodiment 69. The pharmaceutical composition of any one of embodiments 62-68, wherein the dose of the calcium channel blocker is about 66% of the lowest hypertension therapeutic dose (LHTD) for the calcium channel blocker.

Embodiment 70. The pharmaceutical composition of embodiment 69, wherein the calcium channel blocker is amlodipine besylate and dose of amlodipine besylate is about 1.65 mg.

Embodiment 71. The pharmaceutical composition of any one of embodiments 62-70, wherein the dose of the angiotensin II receptor blocker is about 66% of the lowest hypertension therapeutic dose (LHTD) for the angiotensin II receptor blocker.

Embodiment 72. The pharmaceutical composition of embodiment 71, wherein the angiotensin II receptor blocker is irbesartan, and dose of the irbesartan is about 49.5 mg.

Embodiment 73. The pharmaceutical composition of embodiment 71, wherein the angiotensin II receptor blocker is telmisartan, and the dose of the telmisartan is about 13.2 mg.

Embodiment 74. The pharmaceutical composition of embodiment 62, wherein the angiotensin II receptor blocker is irbesartan, the diuretic is hydrochlorothiazide, and the calcium channel blocker is amlodipine besylate.

Embodiment 75. The pharmaceutical composition of embodiment 74, wherein the dose of irbesartan is from about 45 mg to about 60 mg, the dose of hydrochlorothiazide is from about 7.5 mg to about 10 mg, and the dose of amlodipine besylate is from about 1.5 mg to about 2 mg.

Embodiment 76. The pharmaceutical composition of embodiment 75, wherein the dose of irbesartan is about 49.5 mg, the dose of hydrochlorothiazide is about 8.25 mg, and the dose of amlodipine besylate is about 1.65 mg.

Embodiment 77. The pharmaceutical composition of embodiment 62, wherein the angiotensin II receptor blocker is telmisartan, the diuretic is hydrochlorothiazide, and the calcium channel blocker is amlodipine besylate.

Embodiment 78. The pharmaceutical composition of embodiment 77, wherein the dose of telmisartan is from about 12 mg to about 16 mg, the dose of hydrochlorothiazide is from about 7.5 mg to about 10 mg, and the dose of amlodipine besylate is from about 1.5 mg to about 2 mg.

Embodiment 79. The pharmaceutical composition of embodiment 78, wherein the dose of telmisartan is about 13.2 mg, the dose of hydrochlorothiazide is about 8.25 mg, and the dose of amlodipine besylate is about 1.65 mg.

Embodiment 80. The pharmaceutical composition of embodiment 62, wherein the angiotensin II receptor blocker is irbesartan, the diuretic is indapamide, and the calcium channel blocker is amlodipine besylate.

Embodiment 81. The pharmaceutical composition of embodiment 80, wherein the dose of irbesartan is from about 45 mg to about 60 mg, the dose of indapamide is from about 0.75 mg to about 1.0 mg, and the dose of amlodipine besylate is from about 1.5 mg to about 2 mg.

Embodiment 82. The pharmaceutical composition of embodiment 81, wherein the dose of irbesartan is about 49.5 mg, the dose of indapamide is about 0.825 mg, and the dose of amlodipine is about 1.65 mg.

Embodiment 83. The pharmaceutical composition of embodiment 62, wherein the angiotensin II receptor blocker is telmisartan, the diuretic is indapamide, and the calcium channel blocker is amlodipine besylate.

Embodiment 84. The pharmaceutical composition of embodiment 83, wherein the dose of telmisartan is from about 12 mg to about 16 mg, the dose of indapamide is from about 0.75 mg to about 1.0 mg, and the dose of amlodipine besylate is from about 1.5 mg to about 2 mg.

Embodiment 85. The pharmaceutical composition of embodiment 84, wherein the dose of telmisartan is about 13.2 mg, the dose of indapamide is about 0.825 mg, and the dose of amlodipine besylate is about 1.65 mg.

Embodiment 86. The pharmaceutical composition of embodiment 62, wherein the angiotensin II receptor blocker is telmisartan, the diuretic is chlorthalidone, and the calcium channel blocker is amlodipine besylate.

Embodiment 87. The pharmaceutical composition of embodiment 86, wherein the dose of telmisartan is from about 12 mg to about 16 mg, the dose of chlorthalidone is from about 15 mg to about 20 mg, and the dose of amlodipine besylate is from about 1.5 mg to about 2 mg.

Embodiment 88. The pharmaceutical composition of embodiment 87, wherein the dose of telmisartan is about 13.2 mg, the dose of chlorthalidone is about 16.5 mg, and the dose of amlodipine besylate is about 1.65 mg.

Embodiment 89. The pharmaceutical composition of embodiment 62, wherein the angiotensin II receptor blocker is irbesartan, the diuretic is chlorthalidone, and the calcium channel blocker is amlodipine besylate.

Embodiment 90. The pharmaceutical composition of embodiment 89, wherein the dose of irbesartan is from about 45 mg to about 60 mg, the dose of chlorthalidone is from about 15 mg to about 20 mg, and the dose of amlodipine besylate is from about 1.5 mg to about 2 mg.

Embodiment 91. The pharmaceutical composition of embodiment 90, wherein the dose of irbesartan is about 49.5 mg, the dose of chlorthalidone is about 16.5 mg, and the dose of amlodipine besylate is about 1.65 mg.

Embodiment 92. The pharmaceutical composition of any one of embodiments 1-91, wherein the dose of any one of the angiotensin II receptor blocker, the diuretic, and the calcium channel blocker is substituted with from about 80% to about 250% of the lowest hypertension therapeutic dose (LHTD) for the angiotensin II receptor blocker, the diuretic, or the calcium channel blocker.

Embodiment 93. The pharmaceutical composition of embodiment 92, wherein the dose of the angiotensin II receptor blocker is substituted with from about 80% to about 250% of the lowest hypertension therapeutic dose (LHTD) for the angiotensin II receptor blocker.

Embodiment 94. The pharmaceutical composition of embodiment 92, wherein the dose of the diuretic is substituted with from about 80% to about 250% of the lowest hypertension therapeutic dose (LHTD) for the diuretic.

Embodiment 95. The pharmaceutical composition of embodiment 92, wherein the dose of the calcium channel blocker is substituted with from about 80% to about 250% of the lowest hypertension therapeutic dose (LHTD) for the calcium channel blocker.

Embodiment 96. The pharmaceutical composition of any one of embodiments 92-95, wherein the dose of any one of the angiotensin II receptor blocker, the diuretic, and the calcium channel blocker is substituted with from about 80% to about 150% of the lowest hypertension therapeutic dose (LHTD) for the angiotensin II receptor blocker, the diuretic, or the calcium channel blocker.

Embodiment 97. The pharmaceutical composition of embodiment 96, wherein the dose of the angiotensin II receptor blocker is substituted with from about 80% to about 150% of the lowest hypertension therapeutic dose (LHTD) for the angiotensin II receptor blocker.

Embodiment 98. The pharmaceutical composition of embodiment 97, wherein the dose of the angiotensin II receptor blocker is substituted with about 100% of the lowest hypertension therapeutic dose (LHTD) for the angiotensin II receptor blocker.

Embodiment 99. The pharmaceutical composition of embodiment 96, wherein the dose of the diuretic is substituted with from about 80% to about 150% of the lowest hypertension therapeutic dose (LHTD) for the diuretic.

Embodiment 100. The pharmaceutical composition of embodiment 99, wherein the dose of the diuretic is substituted with about 100% of the lowest hypertension therapeutic dose (LHTD) for the diuretic.

Embodiment 101. The pharmaceutical composition of embodiment 96, wherein the dose of the calcium channel blocker is substituted with from about 80% to about 150% of the lowest hypertension therapeutic dose (LHTD) for the calcium channel blocker.

Embodiment 102. The pharmaceutical composition of embodiment 101, wherein the dose of the calcium channel blocker is substituted with about 100% of the lowest hypertension therapeutic dose (LHTD) for the calcium channel blocker.

Embodiment 103. The pharmaceutical composition of any one of embodiments 92-95, wherein the dose of any one of the angiotensin II receptor blocker, the diuretic, and the calcium channel blocker is substituted with from about 150% to about 250% of the lowest hypertension therapeutic dose (LHTD) for the angiotensin II receptor blocker, the diuretic, or the calcium channel blocker.

Embodiment 104. The pharmaceutical composition of embodiment 103, wherein the dose of the angiotensin II receptor blocker is substituted with from about 150% to about 250% of the lowest hypertension therapeutic dose (LHTD) for the angiotensin II receptor blocker.

Embodiment 105. The pharmaceutical composition of embodiment 104, wherein the dose of the angiotensin II receptor blocker is substituted with about 200% of the lowest hypertension therapeutic dose (LHTD) for the angiotensin II receptor blocker.

Embodiment 106. The pharmaceutical composition of embodiment 103, wherein the dose of the diuretic is substituted with from about 150% to about 250% of the lowest hypertension therapeutic dose (LHTD) for the diuretic.

Embodiment 107. The pharmaceutical composition of embodiment 106, wherein the dose of the diuretic is substituted with about 200% of the lowest hypertension therapeutic dose (LHTD) for the diuretic.

Embodiment 108. The pharmaceutical composition of embodiment 103, wherein the dose of the calcium channel blocker is substituted with from about 150% to about 250% of the lowest hypertension therapeutic dose (LHTD) for the calcium channel blocker.

Embodiment 109. The pharmaceutical composition of any embodiment 108, wherein the dose of the calcium channel blocker is substituted with about 200% of the lowest hypertension therapeutic dose (LHTD) for the calcium channel blocker.

Embodiment 110. The pharmaceutical composition of any one of embodiments 1-91, wherein the dose of any two of the angiotensin II receptor blocker, the diuretic, and the calcium channel blocker is substituted with from about 80% to about 250% of the lowest hypertension therapeutic dose (LHTD) for the angiotensin II receptor blocker, the diuretic, or the calcium channel blocker.

Embodiment 111. The pharmaceutical composition of embodiment 110, wherein the dose of the angiotensin II receptor blocker is substituted with from about 80% to about 250% of the lowest hypertension therapeutic dose (LHTD) for the angiotensin II receptor blocker.

Embodiment 112. The pharmaceutical composition of embodiment 110, wherein the dose of the diuretic is substituted with from about 80% to about 250% of the lowest hypertension therapeutic dose (LHTD) for the diuretic.

Embodiment 113. The pharmaceutical composition of embodiment 110, wherein the dose of the calcium channel blocker is substituted with from about 80% to about 250% of the lowest hypertension therapeutic dose (LHTD) for the calcium channel blocker.

Embodiment 114. The pharmaceutical composition of any one of embodiments 110-113, wherein the dose of any two of the angiotensin II receptor blocker, the diuretic, and the calcium channel blocker is substituted with from about 80% to about 150% of the lowest hypertension therapeutic dose (LHTD) for the angiotensin II receptor blocker, the diuretic, or the calcium channel blocker.

Embodiment 115. The pharmaceutical composition of embodiment 114, wherein the dose of the angiotensin II receptor blocker is substituted with from about 80% to about 150% of the lowest hypertension therapeutic dose (LHTD) for the angiotensin II receptor blocker.

Embodiment 116. The pharmaceutical composition of embodiment 115, wherein the dose of the angiotensin II receptor blocker is substituted with about 100% of the lowest hypertension therapeutic dose (LHTD) for the angiotensin II receptor blocker.

Embodiment 117. The pharmaceutical composition of embodiment 114, wherein the dose of the diuretic is substituted with from about 80% to about 150% of the lowest hypertension therapeutic dose (LHTD) for the diuretic.

Embodiment 118. The pharmaceutical composition of embodiment 117, wherein the dose of the diuretic is substituted with about 100% of the lowest hypertension therapeutic dose (LHTD) for the diuretic.

Embodiment 119. The pharmaceutical composition of embodiment 114, wherein the dose of the calcium channel blocker is substituted with from about 80% to about 150% of the lowest hypertension therapeutic dose (LHTD) for the calcium channel blocker.

Embodiment 120. The pharmaceutical composition of embodiment 119, wherein the dose of the calcium channel blocker is substituted with about 100% of the lowest hypertension therapeutic dose (LHTD) for the calcium channel blocker.

Embodiment 121. The pharmaceutical composition of any one of embodiments 110-113, wherein the dose of any two of the angiotensin II receptor blocker, the diuretic, and the calcium channel blocker is substituted with from about 150% to about 250% of the lowest hypertension therapeutic dose (LHTD) for the angiotensin II receptor blocker, the diuretic, or the calcium channel blocker.

Embodiment 122. The pharmaceutical composition of embodiment 121, wherein the dose of the angiotensin II receptor blocker is substituted with from about 150% to about 250% of the lowest hypertension therapeutic dose (LHTD) for the angiotensin II receptor blocker.

Embodiment 123. The pharmaceutical composition of embodiment 122, wherein the dose of the angiotensin II receptor blocker is substituted with about 200% of the lowest hypertension therapeutic dose (LHTD) for the angiotensin II receptor blocker.

Embodiment 124. The pharmaceutical composition of embodiment 121, wherein the dose of the diuretic is substituted with from about 150% to about 250% of the lowest hypertension therapeutic dose (LHTD) for the diuretic.

Embodiment 125. The pharmaceutical composition of embodiment 124, wherein the dose of the diuretic is substituted with about 200% of the lowest hypertension therapeutic dose (LHTD) for the diuretic.

Embodiment 126. The pharmaceutical composition of embodiment 121, wherein the dose of the calcium channel blocker is substituted with from about 150% to about 250% of the lowest hypertension therapeutic dose (LHTD) for the calcium channel blocker.

Embodiment 127. The pharmaceutical composition of any embodiment 126, wherein the dose of the calcium channel blocker is substituted with about 200% of the lowest hypertension therapeutic dose (LHTD) for the calcium channel blocker.

Embodiment 128: A pharmaceutical composition comprising
(a) telmisartan;
(b) a thiazide-like diuretic; and
(c) a calcium channel blocker
wherein the dose of each (a), (b), and (c) is from about 80% to about 150% of the lowest hypertension therapeutic dose (LHTD) for each of the (a), (b), and (c).

Embodiment 129: The pharmaceutical composition of embodiment 128, wherein the pharmaceutical composition is essentially free of an angiotensin-converting enzyme inhibitor or a pharmaceutically acceptable salt thereof, a beta-blocker or a pharmaceutically acceptable salt thereof, a lipid-regulating agent, platelet function-altering agent, a serum homocysteine-lowering agent, or a combination thereof.

Embodiment 130: The pharmaceutical composition of embodiments 128 or 129, wherein the thiazide-like diuretic is quinethazone, clopamide, chlorthalidone, mefruside, clofenamide, metolazone, meticrane, xipamide, indapamide, clorexolone, fenquizone, or the pharmaceutically acceptable salt or hydrate thereof.

Embodiment 131: The pharmaceutical composition of embodiment 130, wherein the thiazide-like diuretic is indapamide or the hydrate thereof.

Embodiment 132: The pharmaceutical composition of embodiment 131, wherein the thiazide-like diuretic is indapamide.

Embodiment 133: The pharmaceutical composition of any one of embodiments 128-132, wherein the calcium channel blocker is amlodipine, nifedipine, diltiazem, nimodipine, verapamil, isradipine, felodipine, nicardipine, nisoldipine, clevidipine, dihydropyridine, lercanidipine, nitrendipine, cilnidipine, manidipine, mibefradil, bepridil, barnidipine, nilvadipine, gallopamil, lidoflazine, aranidipine, dotarizine, diproteverine, or the pharmaceutically acceptable salt or hydrate thereof.

Embodiment 134: The pharmaceutical composition of embodiment 133, wherein the calcium channel blocker is amlodipine or the pharmaceutically acceptable salt thereof.

Embodiment 135: The pharmaceutical composition of embodiment 134, wherein the calcium channel blocker is amlodipine besylate.

Embodiment 136: The pharmaceutical composition of any one of embodiments 128-135, wherein the dose of each (a), (b), and (c) is from about 80% to about 120% of the lowest hypertension therapeutic dose (LHTD) for each of the (a), (b), and (c).

Embodiment 137: The pharmaceutical composition of embodiment 136, wherein the dose of the thiazide-like diuretic is about 100% of the lowest hypertension therapeutic dose (LHTD) for the thiazide-like diuretic.

Embodiment 138: The pharmaceutical composition of embodiment 137, wherein the thiazide-like diuretic is indapamide, and the dose of the indapamide is about 1.25 mg.

Embodiment 139: The pharmaceutical composition of any one of embodiments 136-138, wherein the dose of the calcium channel blocker is about 100% of the lowest hypertension therapeutic dose (LHTD) for the calcium channel blocker.

Embodiment 140: The pharmaceutical composition of embodiment 139, wherein the calcium channel blocker is amlodipine besylate, and the dose of amlodipine besylate is about 2.5 mg.

Embodiment 141: The pharmaceutical composition of any one of embodiments 136-140, wherein the dose of the telmisartan is about 100% of the lowest hypertension therapeutic dose (LHTD) for telmisartan.

Embodiment 142: The pharmaceutical composition of embodiment 141, wherein the dose of the telmisartan is about 20 mg.

Embodiment 143: The pharmaceutical composition of embodiment 136, wherein the thiazide-like diuretic is indapamide, and the calcium channel blocker is amlodipine besylate.

Embodiment 144: The pharmaceutical composition of embodiment 143, wherein the dose of telmisartan is from about 16 mg to about 24 mg, the dose of indapamide is from about 1 mg to about 1.5 mg, and the dose of amlodipine besylate is from about 2 mg to about 3 mg.

Embodiment 145: The pharmaceutical composition of embodiment 143, wherein the dose of telmisartan is about 20 mg, the dose of indapamide is about 1.25 mg, and the dose of amlodipine besylate is about 2.5 mg.

Embodiment 146. The pharmaceutical composition of any one of embodiments 1-145, wherein (a), (b), and (c) are provided in one formulation.

Embodiment 147. The pharmaceutical composition of any one of embodiments 1-145, wherein (a), (b), and (c) are each provided in a separate formulation.

Embodiment 148. The pharmaceutical composition of any one of embodiments 1-145, wherein two of the (a), (b), and (c) are provided in one formulation.

Embodiment 149. The pharmaceutical composition of any one of embodiments 1-148, wherein the pharmaceutical composition is in the form of pill, tablet, or capsule.

Embodiment 150. The pharmaceutical composition of any one of embodiments 1-149, wherein the pharmaceutical composition is suitable for oral administration.

Embodiment 151: A method of treating hypertension in a subject in need thereof comprising administering the pharmaceutical composition of any one of embodiments 1-150.

Embodiment 152. The method of embodiment 151, wherein the treatment results in a systolic blood pressure (SBP) of less than about 140 mmHg.

Embodiment 153. The method of embodiments 150 or 151, wherein the treatment results in a reduction of systolic blood pressure (SBP) of about 10 mmHg or greater.

Embodiment 154. The method of any one of embodiments 150-153, wherein the treatment results in a diastolic blood pressure (DBP) of less than about 90 mmHg.

Embodiment 155. The method of any one of embodiments 150-154, wherein the treatment results in a reduction of diastolic blood pressure (DBP) of about 5 mmHg or greater.

Embodiment 156. The method of any one of embodiments 150-155, wherein treatment results in a reduction in systolic blood pressure (SBP) that is greater than the reduction obtained with the full lowest hypertension therapeutic dose of any one of the (a), (b), and (c) in the pharmaceutical composition.

Embodiment 157. The method of any one of embodiments 150-156, wherein treatment results in a reduction in diastolic blood pressure (DBP) that is greater than the reduction obtained with the full lowest hypertension therapeutic dose of any one of (a), (b), and (c) in the pharmaceutical composition.

Embodiment 158. The method of any one of embodiments 150-157, wherein the treatment results in greater long term tolerability and reduced risk of side effects when compared to treatment with the full lowest hypertension therapeutic dose of any one of (a), (b), and (c) in the pharmaceutical composition.

Embodiment 159. The method of any one of embodiments 150-158, wherein the treatment is the initial or first-line treatment of hypertension.

Embodiment 160. The method of any one of embodiments 150-159, wherein the subject is not receiving any previous hypertension therapy prior to treatment.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A pharmaceutical composition for use in the treatment of hypertension comprising:
    a. telmisartan in an amount from about 8 mg to about 20 mg;
    b. chlorthalidone in an amount from about 10 mg to about 37.5 mg; and
    c. amlodipine besylate in an amount from about 1 mg to about 3.75 mg,
    wherein the pharmaceutical composition is free of a beta-blocker.

2. The pharmaceutical composition of claim 1, wherein telmisartan is in an amount from about 8 mg to about 16 mg, chlorthalidone is in an amount from about 10 mg to about 20 mg, and amlodipine besylate is in an amount from about 1 mg to about 2 mg.

3. The pharmaceutical composition of claim 2, wherein telmisartan is in an amount from about 8 mg to about 12 mg, chlorthalidone is in an amount from about 10 mg to about 15 mg, and amlodipine besylate is in an amount from about 1 mg to about 1.5 mg.

4. The pharmaceutical composition of claim 3, where telmisartan is in an amount of about 10 mg, chlorthalidone is in an amount of about 12.5 mg, and amlodipine besylate is in an amount of about 1.25 mg.

5. The pharmaceutical composition of claim 2, wherein telmisartan is in an amount from about 12 mg to about 16 mg, chlorthalidone is in an amount from about 15 mg to about 20 mg, and amlodipine besylate is in an amount from about 1.5 mg to about 2 mg.

6. The pharmaceutical composition of claim 5, wherein telmisartan is in an amount of about 13.2 mg, chlorthalidone is in an amount of about 16.5 mg, and amlodipine besylate is in an amount of about 1.65 mg.

7. The pharmaceutical composition of claim 1, wherein telmisartan is in an amount from about 16 mg to about 20 mg, chlorthalidone is in an amount from about 20 mg to about 37.5 mg, and amlodipine besylate is in an amount from about 2 mg to about 3.75 mg.

8. The pharmaceutical composition of claim 7, wherein telmisartan is in an amount from about 16 mg to about 20 mg, chlorthalidone is in an amount from about 20 mg to about 30 mg, and amlodipine besylate is in an amount from about 2 mg to about 3 mg.

9. The pharmaceutical composition of claim 8, wherein telmisartan is in an amount of about 20 mg, chlorthalidone is in an amount of about 25 mg, and amlodipine besylate is in an amount of about 2.5 mg.

10. A method of treating hypertension comprising administering the pharmaceutical composition of claim 1 to a subject in need thereof.

11. The pharmaceutical composition of claim 1, wherein said pharmaceutical composition is suitable for oral administration.

12. The pharmaceutical composition of claim 11, wherein said pharmaceutical composition is in the form of a pill, tablet, or capsule.

* * * * *